US008044206B2

(12) United States Patent
Kikuchi et al.

(10) Patent No.: US 8,044,206 B2
(45) Date of Patent: Oct. 25, 2011

(54) NITROGEN—CONTAINING HETEROCYCLIC DERIVATIVES HAVING 2,6-DISUBSTITUTED STYRYL

(75) Inventors: Kazumi Kikuchi, Tokyo (JP); Makoto Oku, Tokyo (JP); Jiro Fujiyasu, Tokyo (JP); Norio Asai, Tokyo (JP); Toshihiro Watanabe, Tokyo (JP); Yukinori Nagakura, Tokyo (JP); Hiroshi Tomiyama, Sakaki-machi (JP); Motoharu Sonegawa, Sakaki-machi (JP); Kazuo Tokuzaki, Sakaki-machi (JP); Yoshinori Iwai, Sakaki-machi (JP)

(73) Assignees: Astellas Pharma Inc., Tokyo (JP); Kotobuki Pharmaceutical Co., Ltd., Nagano (JP)

( * ) Notice: Subject to any disclaimer, the term of this patent is extended or adjusted under 35 U.S.C. 154(b) by 1173 days.

(21) Appl. No.: 10/548,197

(22) PCT Filed: Mar. 5, 2004

(86) PCT No.: PCT/JP2004/002842
§ 371 (c)(1),
(2), (4) Date: Oct. 13, 2006

(87) PCT Pub. No.: WO2004/078715
PCT Pub. Date: Sep. 16, 2004

(65) Prior Publication Data
US 2007/0099956 A1    May 3, 2007

(30) Foreign Application Priority Data
Mar. 7, 2003  (JP) .................................. 2003-061758

(51) Int. Cl.
*C07D 211/08* (2006.01)
*A61K 31/47* (2006.01)

(52) U.S. Cl. ....................................... 546/192; 514/317
(58) Field of Classification Search .................. 546/192; 514/317
See application file for complete search history.

(56) References Cited

U.S. PATENT DOCUMENTS

| 3,658,797 | A | 4/1972 | Ross et al. |
| 4,514,412 | A | 4/1985 | Karjalainen et al. |
| 4,639,452 | A | 1/1987 | Platel et al. |
| 6,784,192 | B2 * | 8/2004 | Ozaki et al. .................. 514/318 |
| 2003/0220368 | A1 | 11/2003 | Ozaki et al. |
| 2004/0167224 | A1 | 8/2004 | Ozaki et al. |
| 2004/0172543 | A1 | 9/2004 | Sato et al. |
| 2008/0070898 | A1 * | 3/2008 | Kikuchi et al. .......... 514/211.15 |

FOREIGN PATENT DOCUMENTS

| EP | 34473 | A2 | 8/1981 |
| EP | 0 072 615 | A1 | 2/1983 |
| EP | 0 279 681 | A2 | 2/1988 |
| EP | 551617 | A2 | 7/1993 |
| EP | 0909564 | A1 | 4/1999 |
| EP | 1180513 | A1 | 2/2002 |
| EP | 1 254 904 | A1 | 11/2002 |
| EP | 1422782 | A1 | 5/2004 |
| EP | 1602645 | A1 | 12/2005 |
| JP | 58-159484 | A | 9/1983 |
| JP | 60-193966 | | 10/1985 |
| JP | 1-316359 | A | 12/1989 |
| JP | 2-179 | | 1/1990 |
| JP | 4-342579 | | 11/1992 |
| JP | 4-342579 | A | 11/1992 |
| JP | 5-213915 | A | 8/1993 |
| JP | 2001-270883 | | * 10/2001 |
| JP | 2002-523448 | T | 7/2002 |
| WO | WO 91/18603 | A1 | 12/1991 |
| WO | WO 93/12110 | A1 | 6/1993 |
| WO | 94/13291 | A1 | 6/1994 |
| WO | WO 95/24390 | A1 | 9/1995 |
| WO | WO 96/13479 | A1 | 5/1996 |
| WO | WO 97/19059 | A1 | 5/1997 |
| WO | 99/02497 | A2 | 1/1999 |
| WO | WO 99/02497 | A2 | 1/1999 |
| WO | WO 99/08678 | A1 | 2/1999 |
| WO | 00/12074 | A2 | 3/2000 |
| WO | WO 01/07436 | A2 | 2/2001 |
| WO | WO 01/16121 | A1 | 3/2001 |
| WO | 01/53288 | A1 | 7/2001 |
| WO | WO 01/53288 | | * 7/2001 |
| WO | WO 01/74796 | A1 | 10/2001 |
| WO | WO 02/46166 | A1 | 6/2002 |
| WO | 02/066484 | A1 | 8/2002 |
| WO | WO 02/102381 | A1 | 12/2002 |
| WO | WO 2004/011430 | | * 2/2004 |
| WO | WO 2004/011430 | A1 | 2/2004 |
| WO | WO 2004/037817 | A1 | 5/2004 |
| WO | 2004/078715 | A1 | 9/2004 |

OTHER PUBLICATIONS

Benedetti, P. et al J. Med. Chem. 2002, 45, 1577-1584.*
Carl Tabb Banner, et al, "4-(4-Dimethylaminostyryl)quinolines with a methyl group on the styryl ring," Journal of Organic Chemistry, vol. 26, No. 7, pp. 2566-2567, 1961.
S.K. Chervenkov, et al, "IR-, $^1$H-NMR and TLC examination of new 2-styrylquinolines with antibacterial activity," Analytical Letters, vol. 28, No. 1, pp. 59-70, 1995.
A. Haddow, et al, "Investigations of tumour-inhibitory styrylquinoline derivatives," Acta Unio Internationalis Contra Cancrum, vol. 16, pp. 489-495, 1960.
John A. Lamberton, et al, "Alkaloids of Peripentadenia mearsii. I. Isolation, Structural Determination, and Synthesis of Peripentadenine," Journal of Natural Products, vol. 46, No. 2, pp. 235-247, 1983.

(Continued)

*Primary Examiner* — Rita J. Desai
*Assistant Examiner* — John Mabry
(74) *Attorney, Agent, or Firm* — Sughrue Mion, PLLC

(57) ABSTRACT

The invention provides a novel nitrogen-containing heterocyclic derivative having 2,6-disubstituted styryl and a pharmaceutically acceptable salt thereof, and a pharmaceutical composition comprising the nitrogen-containing heterocyclic derivative and a pharmaceutically acceptable salt thereof, in particular, a pharmaceutical composition effective as a sodium channel inhibitor, having an excellent analgesic action especially on neuropathic pain with minimized side effects.

8 Claims, No Drawings

OTHER PUBLICATIONS

S. V. Tsukerman, et al, "Synthesis of chalcone analogs from 2-acetylquinoline," Zhurnal Obshchei Khimii, vol. 34, No. 9, pp. 2881-2886, 1964 Abstract.
Supplementary European Search Report dated Nov. 5, 2008.
Yinglin Han, et al., "Total Asymmetric Synthesis of Highly Constrained Amino Acids β-Isopropyl-2',6'-Dimethyl-Tyrosines," *Tetrahedron Letters*, vol. 38, No. 29, pp. 5135-5138, 1997.
Ryszard Gawinecki, et al., "The effect of the amino group on the spectral properties of substituted styrylpyridinium salts," *Dyes and Pigments*, vol. 45, pp. 103-107, 2000.
Beata Jedrzejewska, et al., "Hemicyanine dyes: synthesis, structure and photophysical properties," *Dyes and Pigments*, vol. 58, pp. 47-58, 2003.
Vladimir V. Rozhkov, et al., "Synthesis of 2-Aryl- and 2-Hetaryl-4, 6-dinitroindols from 2, 4, 6-Trinitrotoluene," Synthesis, 1999, No. 12, pp. 2065-2070.
C.T. Bahner, et al., "Di- and Tri-methoxystyryl Derivatives of Heterocyclic Nitrogen Compounds," *Arzneimittel-Forschung*, 1981, vol. 31, No. 3, pp. 404-406.

Office Action issued on Oct. 5, 2010 from the European Patent Office in a counterpart European Application No. 04717835.5.
Cignabella G. et al., "Bicyclic Homologs of Piperazine. VII.1 Synthesis and Analgesic Activity of 3-Aralkenyl-8-propionyl-3,8-diazabicyclo[3.2.1]-octanes", J. Med. Chem. 1965, vol. 8, pp. 326-331.
Japanese Office Action issued on Jul. 5, 2010 from the Japan Patent Office in a counterpart Japanese application No. 2005-503134.
Chinese Office Action issued in CN 2005800293270, dated Jan. 8, 2010.
M. Lamontagne et al., "Antimalarials. 8. Synthesis of Amino Ethers as Candidate Antimalarials," Journal of Medicinal Chemistry, vol. 19, No. 3, pp. 360-365, 1976.
Kikuchi et al "Preparation of nitrogenous . . . " CA141:260786 (2004).
Communication dated Mar. 8, 2011 from the European Patent Office in a counterpart European application (EP 04717835.5).

* cited by examiner

NITROGEN—CONTAINING HETEROCYCLIC DERIVATIVES HAVING 2,6-DISUBSTITUTED STYRYL

This is a U.S. national stage entry of Application No. PCT/JP2004/002842 filed Mar. 5, 2004.

TECHNICAL FIELD

The present invention relates to a novel nitrogen-containing heterocyclic derivative having 2,6-disubstituted styryl and a pharmaceutically acceptable salt thereof. The present invention further relates to a pharmaceutical composition comprising a novel nitrogen-containing heterocyclic derivative having 2,6-disubstituted styryl and a pharmaceutically acceptable salt thereof and more particularly, to a pharmaceutical composition having an analgesic action especially on neuropathic pain which acts as a sodium channel inhibitor.

BACKGROUND ART

A voltage-dependent sodium channel is a protein responsible for the initiation and propagation of action potentials in neurons. The voltage-dependent sodium channel is composed of one larger α subunit with four domains, each consisting of six transmembrane segments, as a common structure and two smaller β subunits. A major part of the channel function is played by α subunit. To date, more than 10 different α subunit subtypes have been known (Goldin A L, Annals of the New York Academy of Sciences 868:38-50, 1999). Each voltage-dependent sodium channel subtype shows distinct distributions in the central and peripheral nerve tissues. These subtypes regulate neural excitability and play an important role in regulating physiological functions in individual tissues. It is also suggested that they are deeply associated with various pathological conditions (Goldin A L, Annual Review of Physiology 63:871-894, 2001).

In recent years, it has become clear that voltage-dependent sodium channels are deeply involved in neural transmission of pain, and sodium channel blockers are expected to be excellent pain therapeutics, especially neuropathic pain therapeutics (Taylor C P, Current Pharmaceutical Design 2: 375-388, 1996).

Neuropathic pain means a pain that results from dysfunction in the central or peripheral neurons and refers to diabetic neuropathic pain, cancer pain, trigeminal neuralgia, phantom limb, post herpetic neuralgia, thalamic pain, etc. The clinical picture of neuropathic pain includes stabbing pain, burning pain, hyperalgesia, allodynia, etc.

In medical scenes, non-steroidal anti-inflammatory drugs, narcotic analgesics such as morphine, etc. are used for the purpose of relieving pain. Recently, antiarrhythmic drugs and anticonvulsants, which are sodium channel blockers, have come to be used as well, for the purpose of relieving pain.

The non-steroidal anti-inflammatory drugs are not completely satisfied in terms of analgesic actions and involve the problem of side effects such as gastrointestinal disturbance or renal disorder. The narcotic analgesics such as morphine are effective for nociceptive pain, but encounter serious side effects on the alimentary, respiratory or central nervous system. In addition, these drugs are generally less effective for neuropathic pain.

The antiarrhythmic drugs such as lidocaine or mexiletine and the anticonvulsants such as carbamazepine, which are sodium channel blockers, have come to be used to relieve pain. Mexiletine has been approved and is available as an anti-diabetic neuropathic pain drug. However, these sodium channel blockers involve problems that they have central side effects such as convulsions or drowsiness, or peripheral side effects such as bradycardia and hence, have difficulty to increase a dose to a sufficient level, resulting in failure to achieve satisfactory analgesic effects.

As above, analgesics that are useful for the treatment of neuropathic pain and are excellent in safety have not been found yet. Accordingly, sodium channel blockers having an excellent analgesic action especially on neuropathic pain with minimized side effects have been desired.

Lidocaine, mexiletine, carbamazepine, etc. mentioned above are reported but do not fall under nitrogen-containing heterocyclic derivatives having styryl group.

Derivatives having a 1-pyridylalkylpiperidine as a basic skeleton are disclosed and have a sodium channel inhibitory activity (Patent Literature 1). In this literature, compounds having 2-cyclohexylmethyloxy-6-fluorophenylethenyl on the piperidine ring as a substituent are disclosed.

Also, compounds containing a mono-substituted phenylethenyl having a halogen or cyclohexylmethyloxy at the 2- or 3-position of a 1-aromatic heterocyclic group-alkylpiperidine ring as a substituent are described (Patent Literature 2).

On the other hand, compounds, not as sodium inhibitors but as metabotropic glutamate receptor (mGluR) inhibitors and analgesics, which are one of therapeutics for various diseases, based on mGluR inhibitory effects are disclosed (Patent Literatures 3-4). Specifically, there are described 2-pyridine compounds having styryl group (Patent Literature 3), thiazole, oxazole, 1,2,4-thiadiazole, 1,2,4-oxadiazole, 1H-1,2,4-triazole, 2-oxo-1,3,4-oxathiazole, 2H-tetrazole, 2-pyridine, pyridinium, pirazine, indolinium, benzothiophene, benzothiazonium, quinoline or quinolium compounds having styryl group (Patent Literature 4), imidazole compounds having styryl group (Patent Literature 5), and imidazole, 1,2,4-triazole or 2H-tetrazole compounds having styryl group (Patent Literature 6), but these compounds are unsaturated heterocyclic compounds having styryl group.

Furthermore, piperidine compounds having benzyl or phenylmethylene based on NMDA/NR2B antagonizing effect are disclosed (Patent Literature 7).

On the other hand, nitrogen-containing heterocyclic derivatives having styryl group, which are formed by combining groups, are disclosed (Patent Literatures 8 and 9) and among these derivatives, only the compounds that phenyl group and a nitrogen-containing heterocyclic ring are combined via a —O-lower alkylene-(Patent Literature 3), a —S-lower alkylene- or a -lower alkylene-C(O)O— are specifically disclosed (Patent Literature 4) but nitrogen-containing heterocyclic derivatives are neither disclosed specifically nor even suggested. Moreover, these derivatives are used as calcium channel antagonists (Patent Literature 8) or for promotion of acetylcholine release (Patent Literature 9) but nothing is disclosed or even suggested on any sodium channel inhibitory activity or any analgesic action.

Patent Literature 1
European Patent Publication No. 1254904
Patent Literature 2
WO03/84948 Pamphlet
Patent Literature 3
WO99/02497 Pamphlet
Patent Literature 4
WO01/16121 Pamphlet
Patent Literature 5
WO02/46166 Pamphlet
Patent Literature 6
WO99/08678 Pamphlet
Patent Literature 7

WO01/32615 Pamphlet
Patent Literature 8
WO94/13291 Pamphlet
Patent Literature 9
WO97/19059 Pamphlet

DISCLOSURE OF THE INVENTION

An object of the present invention is to provide a novel nitrogen-containing heterocyclic derivative having 2,6-disubstituted styryl or a pharmaceutically acceptable salt thereof.

Another object of the present invention is to provide a pharmaceutical composition, especially a pharmaceutical composition for a sodium channel inhibitor, which has a remarkable analgesic action on neuropathic pain, comprising the nitrogen-containing heterocyclic derivatives having 2,6-disubstituted styryl or a pharmaceutically acceptable salt thereof and a pharmaceutically acceptable carrier.

The present inventors made extensive studies on nitrogen-containing heterocyclic derivatives to achieve the foregoing objects and as a result, have found that derivatives containing a nitrogen-containing hetero ring having 2,6-disubstituted styryl as a basic skeleton or salts thereof possess a potent inhibitory activity against sodium channel and exert an action on mice with streptozotocin-induced diabetic neuropathy as disease animal models, and have accomplished the present invention, which is useful for neuropathic pain drugs.

That is, the present invention relates to the nitrogen-containing heterocyclic derivatives represented by formula (I) below. The nitrogen-containing heterocyclic derivatives of the present invention are characterized in comprising styryl group always having two substituents at the ortho-position, namely, 2,6-disubstituted styryl group, and a nitrogen-containing heterocyclic group.

This styryl group may optionally have an additional substituent(s). In the nitrogen-containing heterocyclic derivatives, saturated nitrogen-containing heterocyclic derivatives are preferred.

Specifically, the present invention provides the following nitrogen-containing heterocyclic derivatives or pharmaceutically acceptable salts thereof, pharmaceutical compositions comprising these compounds and pharmaceutically acceptable carriers, use of these compounds, a method for treating diseases mediated by sodium channel, a method for treating neuropathic pain, and a method for treating diabetic neuropathic pain.

[1] A nitrogen-containing heterocyclic derivative represented by formula (I) below:

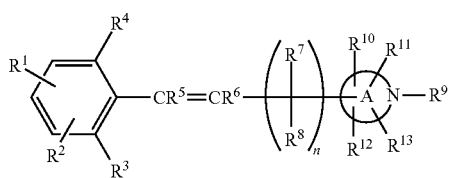

(I)

(wherein symbols in formula (I) above have the following significance:

$R^1$ and $R^2$, which may be the same or different, represent H—, an optionally substituted lower alkyl, a cycloalkyl, an aryl, an acyl, HO—CO—, a lower alkyl-O—CO—, $H_2N$—CO—, a lower alkyl-HN—CO—, a (lower alkyl)$_2$N—CO—, HO—, a lower alkyl-O—, an aryl-O—, an acyl-O—, $H_2N$—, a lower alkyl-HN—, a (lower alkyl)$_2$N—, an acyl-NH—, a halogen, nitro, a heterocyclic group, or cyano;

$R^3$ and $R^4$, which may be the same or different, represent an optionally substituted lower alkyl, a cycloalkyl, an acyl, HO—CO—, a lower alkyl-O—CO—, $H_2N$—CO—, a lower alkyl-HN—CO—, a (lower alkyl)$_2$N—CO—, HO—, a lower alkyl-O—, an acyl-O—, $H_2N$—, a lower alkyl-HN—, a (lower alkyl)$_2$N—, an acyl-NH—, a halogen, nitro, or cyano;

$R^5$ and $R^6$, which may be the same or different, represent H—, a lower alkyl, or a halogen;

$R^7$ and $R^8$, which may be the same or different, represent H—, a lower alkyl, HO—, a lower alkyl-O—, or a halogen;

$R^7$ and $R^8$ may be combined together to form oxo (O=);

$R^9$ represents H—, an optionally substituted lower alkyl, an optionally substituted cycloalkyl, an optionally substituted acyl, a lower alkyl-C (=NH)—, HO—CO—, an optionally substituted lower alkyl-O—CO—, $H_2N$—CO—, an optionally substituted lower alkyl-HN—CO—, an (optionally substituted lower alkyl)$_2$N—CO—, $H_2NC$(=NH)—, $H_2NC$(=NCN)—, $H_2NC$(=N—CONH$_2$)—, $H_2NC$(=NS(=O)$_2$NH$_2$)—, an optionally substituted lower alkyl-SO$_2$— or an optionally substituted heterocyclic group-SO$_2$—;

$R^{10}$, $R^{11}$, $R^{12}$ and $R^{13}$, which may be the same or different, represent H—, or a lower alkyl, and two groups from $R^{10}$, $R^{11}$, $R^{12}$ and $R^{13}$ may be combined together to form oxo (O=);

A represents a nitrogen-containing heterocyclic group, quinolyl or pyridin-4-yl;

provided that when A represents quinolyl or pyridin-4-yl, $R^9$ is absent; and, n represents 0, 1, or 2), or a pharmaceutically acceptable salt thereof.

[2] The nitrogen-containing heterocyclic derivative according to [1], or a pharmaceutically acceptable salt thereof, wherein the nitrogen-containing heterocyclic group shown by symbol A in the formula (I) is a nitrogen-containing saturated monocyclic heterocyclic group or a nitrogen-containing saturated bridged ring.

[3] The nitrogen-containing heterocyclic derivative according to [2], or a pharmaceutically acceptable salt thereof, wherein the nitrogen-containing heterocyclic group shown by symbol A in the formula (I) is a nitrogen-containing saturated monocyclic heterocyclic group.

[4] The nitrogen-containing heterocyclic derivative according to [3], or a pharmaceutically acceptable salt thereof, wherein the nitrogen-containing heterocyclic group shown by symbol A in the formula (I) is a 6-membered nitrogen-containing saturated monocyclic heterocyclic group.

In the nitrogen-containing heterocyclic derivatives or pharmaceutically acceptable salts thereof according to [1] to [4], preferably the nitrogen-containing saturated heterocyclic group shown by symbol A in the formula (I) is piperidine.

[5] The nitrogen-containing heterocyclic derivative according to any one of [1] through [4], or a pharmaceutically acceptable salt thereof, wherein symbols $R^7$ and $R^8$ in the formula (I) above, which may be the same or different, represent H—, a lower alkyl, HO—, a lower alkyl-O—, or a halogen.

[6] The nitrogen-containing heterocyclic derivative according to any one of [1] through [5], or a pharmaceutically acceptable salt thereof, wherein symbol n in the formula (I) is 0.

[7] The nitrogen-containing heterocyclic derivative according to any one of [1] through [6], or a pharmaceutically acceptable salt thereof, wherein symbol $R^9$ in the formula (I) is H.

[8] The nitrogen-containing heterocyclic derivative according to any one of [1] through [6], or a pharmaceutically acceptable salt thereof, wherein symbol $R^9$ in the formula (I) is an optionally substituted lower alkyl.

[9] The nitrogen-containing heterocyclic derivative according to [8], or a pharmaceutically acceptable salt thereof, wherein the substituent in the optionally substituted lower alkyl shown by symbol $R^9$ in the formula (I) is at least one substituent selected from Group a below:

Group a: (1) a halogen, (2) HO, (3) a lower alkyl-O—, (4) $H_2N$, (5) a lower alkyl-NH—, (6) a (lower alkyl)$_2$N—, (7) an aryl and (8) a heterocyclic group; this heterocyclic group is preferably a monocyclic heterocyclic group.

[10] The nitrogen-containing heterocyclic derivative according to any one of [1] through [6], or a pharmaceutically acceptable salt thereof, wherein symbol $R^9$ in the formula (I) is an optionally substituted acyl.

[11] The nitrogen-containing heterocyclic derivative according to [10], or a pharmaceutically acceptable salt thereof, wherein the optionally substituted acyl shown by symbol $R^9$ in the formula (I) is an optionally substituted lower alkyl-CO—, an optionally substituted cycloalkyl-CO—, an optionally substituted aryl-CO—, an optionally substituted heterocyclic group-CO— or an optionally substituted heterocyclic group-lower alkyl-CO—.

[12] The nitrogen-containing heterocyclic derivative according to [10] or [11], or a pharmaceutically acceptable salt thereof, wherein the substituent in the optionally substituted acyl shown by symbol $R^9$ in the formula (I) is at least one substituent selected from Group b below:

Group b: (1) HO, (2) a lower alkyl-O—, (3) $R^{101}R^{102}N$ (wherein $R^{101}$ and $R^{102}$, which may be the same or different, represent (i) H, (ii) a lower alkyl which may optionally be substituted with HO, a lower alkyl-O—, $NH_2$, $H_2N$—CO—, an acyl-NH—, a lower alkyl-NH—, a cycloalkyl, a HO-cycloalkyl, a heterocyclic group or a (lower alkyl)$_2$N—, (iii) an acyl, (iv) a lower alkyl-O—CO—, (v) a heterocyclic group, or (vi) an aryl which may optionally be substituted with a halogen), (4) a halogen, (5) oxo (O═), (6) a cycloalkyl which may be optionally substituted with $R^{101}R^{102}N$, (7) an aryl, (8) a heterocyclic group, (9) a lower alkyl which may optionally be substituted with HO, a lower alkyl-O—, an aryl, an acyl or a heterocyclic group, (10) an acyl which may optionally be substituted with oxo (O═), (11) $H_2N$—CO—, (12) a lower alkyl-SO$_2$—, and (13) a heterocyclic group-SO$_2$—.

[13] The nitrogen-containing heterocyclic derivative according to any one of [1] through [6], or a pharmaceutically acceptable salt thereof, wherein symbol $R^9$ in the formula (I) is HO—OC—, an optionally substituted lower alkyl-O—CO—, $H_2N$—CO—, an optionally substituted lower alkyl-NH—CO—, an (optionally substituted lower alkyl)$_2$N—CO— or an optionally substituted lower alkyl-SO$_2$—.

In the nitrogen-containing heterocyclic derivatives or pharmaceutically acceptable salts thereof according to any one of [1] through [13], symbols $R^4$ and $R^5$ in the formula (I) above are more preferably a lower alkyl, and most preferably, these $R^4$ and $R^5$ are methyl group.

[14] The nitrogen-containing heterocyclic derivative according to [1], or a pharmaceutically acceptable salt thereof, which is at least one compound selected from the group consisting of:
4-[(E)-2-(2,6-dimethylphenyl)vinyl]quinuclidine,
4-[(E)-2-(2-chloro-6-methylphenyl)vinyl]piperidine,
4-[(Z)-2-(2,6-dimethylphenyl)vinyl]piperidine,
4-[(E)-2-(2,6-dimethylphenyl)vinyl]piperidine,
3,5-dimethyl-4-[(E)-2-piperidin-4-ylvinyl]benzonitrile,
N,N,3,5-tetramethyl-4-[(E)-2-piperidin-4-ylvinyl]aniline,
2-[(E)-2-(2,6-dimethylphenyl)vinyl]piperidine,
4-[(E)-2-(2,6-dimethylphenyl)vinyl]azepane,
4-[(2E)-3-(2,6-dimethylphenyl)prop-2-en-1-yl]piperidine,
3-[(E)-2-(2,6-dimethylphenyl)vinyl]-1-methylpiperidine,
1-benzyl-4-[(E)-2-(2,6-dimethylphenyl)vinyl]piperidine,
(2-{4-[(E)-2-(2,6-dimethylphenyl)vinyl]piperidin-1-yl}ethyl)dimethylamine,
5-({4-[(E)-2-(2,6-dimethylphenyl)vinyl]piperidin-1-yl}carbonyl)-1H-1,2,4-triazol-3-amine,
4-(2-{4-[(E)-2-(2,6-dimethyl-4-phenoxyphenyl)vinyl]piperidin-1-yl}-2-oxoethyl) morpholine,
4-(2-{2-[(E)-2-(2,6-dimethylphenyl)vinyl]piperidin-1-yl}-2-oxoethyl)morpholine,
1-(2-{4-[(E)-2-(2,6-dimethylphenyl)vinyl]piperidin-1-yl}-2-oxoethyl)-4-(pyridin-3-ylcarbonyl)piperazine,
(2-{4-[(E)-2-(2,6-dimethylphenyl)vinyl]piperidin-1-yl}-1,1-dimethyl-2-oxoethyl)amine,
[1-({4-[(E)-2-(2,6-dimethylphenyl)vinyl]piperidin-1-yl}carbonyl)cyclobutyl]amine,
4-[(E)-2-(2,6-dimethylphenyl)vinyl]-1-[(2S)-pyrolidin-2-ylcarbonyl]piperidine,
4-[(E)-2-(2,6-dimethylphenyl)vinyl]-1-(1H-imidazol-1-ylacetyl)piperidine,
N-(2-{4-[(E)-2-(2,6-dimethylphenyl)vinyl]piperidin-1-yl}-2-oxoethyl)oxetane-3-amine,
N-{2-[(2-[4-[(E)-2-(2,6-dimethylphenyl)vinyl]piperidin-1-yl]-2-oxoethyl)amino]ethyl}acetamide,
2-[(2-{4-[(E)-2-(2,6-dimethylphenyl)vinyl]piperidin-1-yl}-2-oxoethyl)amino]ethanol,
1-(2-{4-[(E)-2-(2,6-dimethylphenyl)vinyl]piperidin-1-yl}-2-oxoethyl)piperidine-2-carboxamide,
1-(2-{4-(E)-2-(2,6-dimethylphenyl)vinyl]piperidin-1-yl}-2-oxoethyl)-3,5-dimethyl piperidine,
4-[(E)-2-(2,6-dimethylphenyl)vinyl]-1-[(4-pyrolidin-1-ylpiperidin-1-yl)acetyl]piperidine,
4-(2-{4-[(E)-2-(2,6-dimethylphenyl)vinyl]piperidin-1-yl}-2-oxoethyl)morpholine,
[4-(2-{4-[(E)-2-(2,6-dimethylphenyl)vinyl]piperidin-1-yl}-2-oxoethyl)morpholine-2-yl]methanol,
4-(2-{4-[(E)-2-(2,6-dimethylphenyl)vinyl]piperidin-1-yl}-2-oxoethyl)-1,4-oxazepane,
1-(2-{4-[(E)-2-(2,6-dimethylphenyl)vinyl]piperidin-1-yl}-2-oxoethyl)piperidine-4-amine,
1-(2-{4-[(E)-2-(2,6-dimethylphenyl)vinyl]piperidin-1-yl}-2-oxoethyl)piperazine,
(1R,4R)-2-(2-{4-[(E)-2-(2,6-dimethylphenyl)vinyl]piperidin-1-yl}-2-oxoethyl)-2,5-diazabicyclo[2.2.1]heptane, and,
(2-{4-[(E)-2-(2,6-dimethylphenyl)vinyl]piperidin-1-yl}-2-oxoethyl)methyl[(3R)-tetrahydrofuran-3-yl]amine.

[15] A pharmaceutical composition comprising the nitrogen-containing heterocyclic derivative according to any one of [1] through [14], or a pharmaceutically acceptable salt thereof, and a pharmaceutically acceptable carrier.

[16] The pharmaceutical composition according to [15], which is a sodium channel inhibitor.

[17] The pharmaceutical composition according to [15] or [16], which is a therapeutic agent for neuropathic pain.

[18] The pharmaceutical composition according to [17], which is a therapeutic agent for diabetic neuropathic pain.

[19] Use of the nitrogen-containing heterocyclic derivative according to any one of [1] through [14], or a pharmaceutically acceptable salt thereof, to manufacture a pharmaceutical composition.

[20] Use of the nitrogen-containing heterocyclic derivative according to [19], or a pharmaceutically acceptable salt thereof, to manufacture a therapeutic agent for neuropathic pain.

[21] Use of the nitrogen-containing heterocyclic derivative according to [20], or a pharmaceutically acceptable salt thereof, to manufacture a therapeutic agent for diabetic neuropathic pain.

[22] A method for treating a disease caused by sodium channel, which comprises administering to a patient a therapeutically effective dose of the nitrogen-containing heterocyclic derivative according to any one of [1] through [12], or a pharmaceutically acceptable salt thereof.

[23] A method for treating neuropathic pain, which comprises administering to a patient a therapeutically effective dose of the nitrogen-containing heterocyclic derivative according to [22], or a pharmaceutically acceptable salt thereof

[24] A method for treating diabetic neuropathic pain, which comprises administering to a patient a therapeutically effective dose of the nitrogen-containing heterocyclic derivative according to [23], or a pharmaceutically acceptable salt thereof.

BEST MODE FOR CARRYING OUT THE INVENTION

The compounds of the present invention represented by formula (I) (hereinafter sometimes merely referred to as "Compound (I) of the present invention") will be described below in detail.
[Definition, Etc.]
In the definitions of the structural formulae in the specification, the term "lower" is used to mean a straight or branched carbon chain having the carbon number of 1 to 6, unless otherwise indicated.

Examples of The "lower alkyl", for example, is used to mean methyl, ethyl, propyl, isopropyl, butyl, isobutyl, sec-butyl, tert-butyl, pentyl, isopentyl, neopentyl, tert-pentyl, hexyl, isohexyl, and the like, preferably, methyl, ethyl, propyl, butyl and tert-butyl.

The "lower alkenyl" is used to mean a hydrocarbon group having at least one double bond and includes, for example, vinyl, propenyl, allyl, isopropenyl, hexenyl, and the like.

The "lower alkynyl" is used to mean a hydrocarbon group having at least one triple bond and includes, for example, ethynyl, propynyl, butynyl, and the like.

The "cycloalkyl" is used to mean a 1- to 3-ring aliphatic saturated hydrocarbon group having the carbon number of 3 to 14 and includes, for example, cyclopropyl, cyclobutyl, cyclopentyl, cyclohexyl, cycloheptyl, cyclooctyl, bicycloheptyl, bicyclooctyl, bicyclononyl, bicyclodecanyl, tricyclononyl, tricyclodecanyl, tricycloundecanyl, tricyclododecanyl, bicyclo[2.2.1]heptyl, bicyclo[2.2.2]octyl, and the like, preferably, cyclopropyl, cyclobutyl, cyclopentyl, cyclohexyl, cycloheptyl and cyclooctyl.

The "aryl" is used to mean a 1- to 3-ring aromatic hydrocarbon group having the carbon number of 6 to 14, in which a cycloalkyl may optionally be fused to a phenyl. The aryl includes, for example, phenyl, indenyl, naphthyl, anthryl, phenanthryl, indanyl, tetrahydronaphthyl, and the like, preferably, phenyl and naphthyl.

The "heterocyclic group" is used to mean a 4- to 16-membered monocyclic, bicyclic or tricyclic saturated or unsaturated ring containing 1 to 4 hetero atoms selected from N, S and O. This heterocyclic group may optionally be bridged or may optionally take a spiro form. The unsaturated ring includes an aromatic ring (hetero aryl) and a non-aromatic ring. The monocyclic group includes azetidinyl, oxetanyl, pyrrolidinyl, tetrahydrofuranyl, 1,3-dioxoranyl, tetrahydro-2H-pyranyl, pyrazolidinyl, piperazinyl, piperidinyl, morpholinyl, thiomorpholinyl, 1,4-oxazepanyl, trithianyl, dioxoranyl, furyl, thienyl, pyrrolyl, 2,5-dihydro-1H-pyrrol-1-yl, imidazolyl, pyrazolyl, thiazolyl, oxazolyl, pyridyl, pirazinyl, pyrimidyl, triazolyl, thiadiazolyl, pyridazinyl, triazinyl, tetrahydropyranyl, oxadiazolyl, and the like; the bicyclic group includes indolinyl, isoindolinyl, 3,4-methylenedioxyphenyl, 3,4-ethylenedioxyphenyl, benzofuranyl, benzothienyl, benzothiadiazolyl, benzothiazolyl, benzimidazolyl, indolyl, 2,3-dihydroindolyl, quinolyl, isoquinolyl, 1,2,3,4-tetrahydroquinolyl, decahydroquinolyl, 1,2,3,4-tetrahydroisoquinolyl, decahydroisoquinolyl, quinoxalinyl, and the like; and the tricyclic group includes carbazolyl, acridinyl, phenothiadinyl, and the like. The bridged heterocyclic group includes quinuclidinyl, 2,5-diazabicyclo[2.2.1]heptyl, 8-azabicyclo[3.2.1]octyl, 7-azabicyclo[2.2.1]heptyl, and the like. The spiro-heterocyclic group includes 1,4-dioxa-8-azaspiro[4.5]decanyl, and the like.

The "nitrogen-containing hetero-aryl" is used to mean a 4- to 10-membered mono- or bicyclic nitrogen-containing hetero-aryl having 1 to 3 nitrogen atoms in the heterocyclic groups described above and includes, for example, pyrrolyl, imidazolyl, pyrazolyl, triazolyl, tetrazolyl, pyridyl, pyridazyl, pyrimidyl, pyrazyl, triazyl, indolyl, isoindolyl, benzimidazolyl, benzopyrazolyl, pyrrolopyridyl, imidazopyridyl, quinolyl, isoquinolyl, quinoxalyl, and the like, preferably, imidazolyl, pyridyl and quinolyl.

The "nitrogen-containing saturated heterocyclic group" is used to mean a 3- to 10-membered mono- or bicyclic nitrogen-containing heterocycloalkyl having 1 to 3 nitrogen atoms in the heterocyclic groups described above and includes, for example, aziridinyl, azetidinyl, pyrrolidyl, piperidyl, piperazyl, morpholinyl, hexahydroazepinyl, 1,4-diazepinyl, 1,4-oxazepinyl, quinuclidinyl, 2,5-diazabicyclo[2.2.1]heptane, azabicyclooctyl (e.g., azabicyclo[3.2.1]octyl), diazabicyclooctyl, azabicyclononyl, azabicyclodecanyl, 1,4-dioxa-8-azaspiro[4.5]decanyl, and the like, preferably, pyrrolidyl, piperidyl, piperazyl, morpholinyl, hexahydroazepinyl, 1,4-diazepinyl, 1,4-oxazepinyl, quinuclidinyl, 2,5-diazabicyclo[2.2.1]heptane and azabicyclo[3.2.1]octyl.

The "nitrogen-containing heterocyclic group" is used to mean the nitrogen-containing hetero-aryl described above, the nitrogen-containing saturated heterocyclic group described above, or a group formed by fusing the nitrogen-containing heterocyclic group or the nitrogen-containing hetero-aryl and the nitrogen-containing heterocycloalkyl, and preferably means pyrrolidyl, piperidyl, morpholinyl, hexahydroazepinyl, azabicyclo[3.2.1]octyl, 1,4-dioxa-8-azaspiro[4.5]decanyl, imidazolyl, pyridyl and quinolyl.

The "acyl" includes HCO—, a lower alkyl-CO—, a lower alkenyl-CO—, a cycloalkyl-CO—, aryl-CO—, a heterocyclic group-CO—, a heterocyclic group-lower alkyl-CO—, a heterocyclic group-lower alkenyl-CO—, a heterocyclic group-lower alkynyl-CO—, a lower alkyl-CS—, a lower alkenyl-CS—, a cycloalkyl-CS—, an aryl-CS—, heterocyclic group-CS—, a heterocyclic group-lower alkyl-CS—, a heterocyclic group-lower alkenyl-CS— and a heterocyclic group-lower alkynyl-CS—. Preferably, the acyl is a lower alkyl-CO—, a cycloalkyl-CO—, an aryl-CO—, a heterocyclic group-CO— and a heterocyclic group-lower alkyl-CO—. This heterocyclic group-CO— is more preferably a monocyclic heterocyclic group-CO—. Specific examples are HCO—, acetyl, propionyl, cyclopropylcarbonyl, cyclobutylcarbonyl, cyclopentylcarbonyl, cyclohexylcarbonyl, azetidin-2-ylcarbonyl, 2,5-dihydro-1H-pyrrol-1-ylmethylcarbonyl, pyrolidin-2-ylcarbonyl, pyrolidin-1-ylmethylcarbonyl, piperidin-2-ylcarbonyl, piperidin-3-ylcarbonyl, piperidin-4-ylcarbonyl, morpholin-2-ylcarbonyl, morpholin-3-ylcarbonyl, morpholin-4-ylmethylcarbonyl, 1,4-oxazepan-4-yl-carbonyl, 1,4-oxazepan-4-yl-methylcarbonyl, piperidin-1-ylmethylcarbonyl, benzoyl, imidazol-4-ylcarbonyl, imidazol-1-ylmethylcarbonyl, 1,2,4-triazol-2-ylcarbonyl, pyridin-2-ylcarbonyl, nicotinoyl, pyridin-2-ylmethylcarbonyl, isonicotinoyl, benzimidazol-5-ylcarbonyl, thenoyl, pyrrolidinylcarbonyl, piperidinylcarbonyl, 2,5-diazabicyclo[2.2.1]heptan-1-ylmethylcarbonyl, etc.

The "halogen" includes fluoro, chloro, bromo and iodo, preferably, fluoro and chloro.

The substituent in the "optionally substituted lower alkyl" and "optionally substituted cycloalkyl" includes at least one member selected from Group a. The substituent in the "optionally substituted acyl," "optionally substituted lower alkyl-$SO_2$—" and "optionally substituted heterocyclic group-$SO_2$—" includes at least one member selected from Group b.

Group a: (1) halogen, (2) HO, (3) a lower alkyl-O—, (4) $H_2N$, (5) a lower alkyl-NH—, (6) a (lower alkyl)$_2$N—, (7) an aryl and (8) a heterocyclic group; this heterocyclic group is preferably a monocyclic heterocyclic group.

Group b: (1) HO, (2) a lower alkyl-O—, (3) $R^{101}R^{102}N$ (wherein $R^{101}$ and $R^{102}$, which may be the same or different, represent (i) H, (ii) a lower alkyl which may optionally be substituted with HO, lower alkyl-O—, $NH_2$, $H_2N$—CO—, an acyl-NH—, a lower alkyl-NH—, a cycloalkyl, a HO-cycloalkyl, a heterocyclic group or a (lower alkyl)$_2$N—, (iii) an acyl, (iv) a lower alkyl-O—CO—, (v) a heterocyclic group, or (vi) an aryl which may optionally be substituted with a halogen), (4) a halogen, (5) oxo (O=), (6) a cycloalkyl may optionally be substituted with $R^{101}R^{102}N$, (7) an aryl, (8) a heterocyclic group, (9) a lower alkyl which may optionally be substituted with HO, a lower alkyl-O—, an aryl, an acyl or a heterocyclic group, (10) an acyl which may optionally be substituted with oxo (O=), (11) $H_2N$—CO—, (12) a lower alkyl-$SO_2$—, and (13) a heterocyclic group-$SO_2$—.

In Compound (I) of the present invention, optical isomers (enantiomers, diastereomers, etc.) or geometrical isomers are present depending upon type of substituents. Consequently, Compound (I) of the present invention includes these optical isomers or geometrical isomers, either in the isolated form or as mixtures thereof.

Compound (I) of the present invention may form a salt with an acid addition salt or with a base. Specific examples of such acid addition salts with an inorganic acid such as hydrochloric acid, hydrobromic acid, hydroiodic acid, sulfuric acid, nitric acid, phosphoric acid, etc.; with an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid, etc.; with an inorganic base such as sodium, potassium, magnesium, calcium, aluminum, etc., an organic base such as methylamine, ethylamine, monoethanolamine, diethanolamine, triethanolamine, cyclohexylamine, lysine, ornithine, etc. In addition, Compound (I) of the present invention or its pharmaceutically acceptable salts may form hydrates, solvates with ethanol, etc. or polymorphism.

Furthermore, Compound (I) of the present invention includes all of so-called prodrugs, i.e., the compounds which can be metabolized in vivo and converted into Compound (I) of the present invention or its pharmaceutically acceptable salts. Examples of the group which forms the prodrugs of Compound (I) of the present invention are those described in Prog. Med. 5: 2157-2161 (1985) and those described in "Iyakuhin no Kaihatsu" (Development of Pharmaceuticals) published in 1990 by Hirokawa Shoten, Vol. 7, "Molecular Design", pages 163-198. Specifically, the group is a group, which can be converted into the primary amine or secondary amine, HO—, HO—CO—, etc. defined in the present invention. by hydrolysis or solvolysis or under physiological conditions. The prodrugs of HO— include, for example, an optionally substituted lower alkyl-COO—, an optionally substituted aryl-CO—O—, RO—CO-optionally substituted lower alkylene-CO—O— (wherein R represents H— or a lower alkyl; hereinafter the same), RO—CO-optionally substituted lower alkenylene-CO—O—, a RO—CO-lower alkylene-O-lower alkylene-CO—O—, RO—CO—CO—O—, ROS(=O)$_2$-optionally substituted lower alkenylene-CO—O—, phthalidyl-O—, 5-methyl-1,3-dioxolen-2-on-4-yl-methyloxy, etc.

[Processes for Production]

Compound (I) of the present invention can be produced by applying a variety of synthesis techniques, using the characteristics based on its basic skeleton or type of substituents. Hereinafter, representative processes are described below.

Process 1:

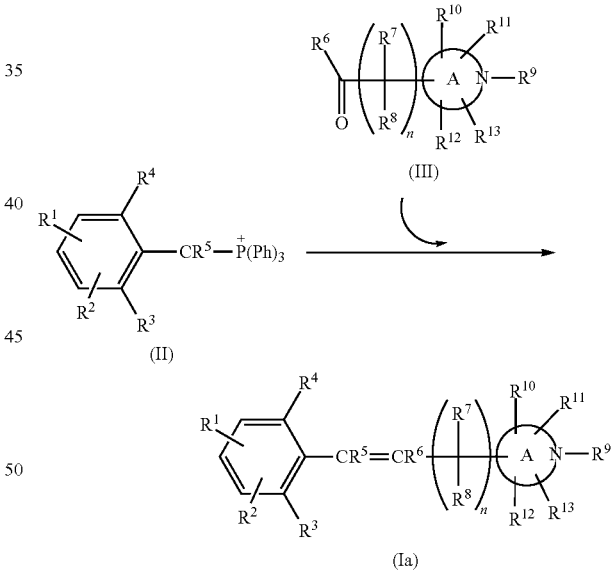

(wherein A, $R^1$-$R^{13}$ and n have the same significance as defined above; hereinafter the same).

Compound (Ia) of the present invention can be obtained by the Wittig reaction (Org. React., 14, 270-490 (1965)) of a phosphonium salt (II) with an aldehyde or ketone (III) in a conventional manner. A reaction solvent, which can be used, includes a solvent inert to this reaction, such as tetrahydrofuran, dioxane, dimethylformamide, dimethylsulfoxide, toluene, etc. As a base, there may be used sodium hydride, potassium tert-butoxide, sodium ethoxide, lithium diisopropylamide, etc. The reaction can be carried out under the conditions of cooling (e.g., −70° C.) to heating.

Process 2:

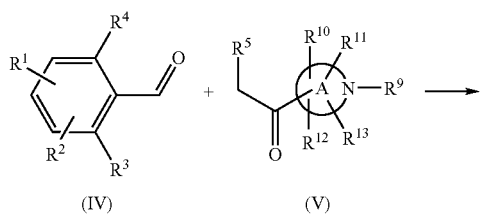

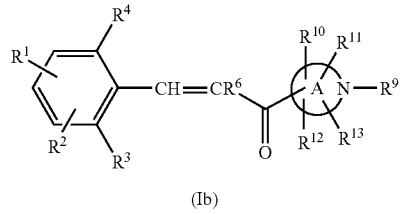

Compound (Ib) of the present invention can be obtained by the aldol condensation (Org. React., 16, 1-438 (1968)) of an aldehyde (IV) with a (V) in a conventional manner. A reaction solvent, which can be used, includes a solvent inert to this reaction, such as tetrahydrofuran, dioxane, dimethylformamide, dimethylsulfoxide, toluene, etc. The reaction may be carried out under basic conditions and in this case, sodium hydride, potassium tert-butoxide, sodium ethoxide, lithium diisopropylamide, lithium bis(trimethylsilyl)amide, etc. may be used. As an acid used when the reaction is carried out under acidic conditions, there may be used hydrochloric acid, trifluoroacetic acid, tosylic acid, boron trifluoride, aluminum trichloride, titanium tetrachloride, etc. The reaction can be carried out under the conditions of cooling (e.g., −70° C.) to heating.

Process 3:

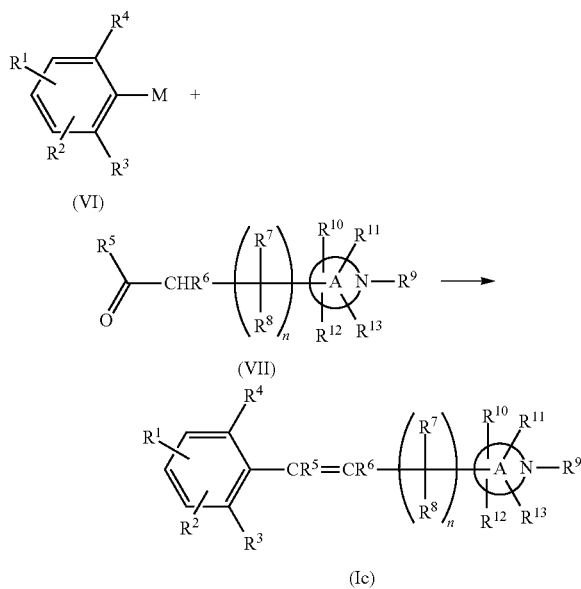

(wherein M represents Li, MgCl, etc.; hereinafter the same).

Compound (Ic) of the present invention can be obtained by the reaction of an aryl metal such as an aryl lithium, an aryl Grignard, etc. with a carbonyl compound in a conventional manner (Org. Synth. III, 200 (1955); Org. React., 6, 339-366 (1964); Org. React., 8, 258-304 (1967)). A reaction solvent, which can be used, includes a solvent inert to this reaction, such as diethyl ether, tetrahydrofuran, dioxane, dimethylsulfoxide, toluene, etc. The reaction can be carried out under the conditions of cooling (e.g., −70° C.) to heating.

In addition to the processes described above, Compound (I) of the present invention can also be obtained, e.g., by the Peterson reaction (Org. React., 38, 1-223 (1990)), formation of triple bond followed by partial reduction (J. Am. Chem. Soc., 77, 3378 (1955); J. Am. Chem. Soc., 99, 2805 (1977); Synthesis, 1973, 457; Tetrahedron 30, 3817 (1974)), etc.

Process 4 (Alkylation):

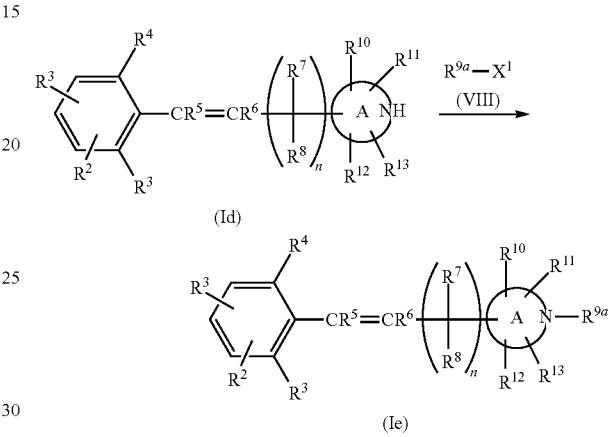

(wherein $R^{9a}$ means $R^9$ other than H and $X^1$ means a leaving group such as a halogen, methanesulfonyloxy, p-toluenesulfonyloxy, etc.; hereinafter the same.)

This process is alkylation. Specifically, the alkylation is carried out as in the processes described above, e.g., in a solvent inert to the reaction, using an amine (Id) and a compound (VIII) having a leaving group corresponding to the reaction in a chemically equivalent amount or in an excess of either reactant, under the conditions of cooling to heating. In some occasions, the reaction is carried out smoothly in the presence of a base (e.g., an inorganic base such as potassium carbonate, sodium carbonate, cesium carbonate, etc.; an organic base such as triethylamine, diisopropylethylamine, etc.; a metal alkoxides such as potassium tert-butoxide, sodium tert-butoxide, etc.; sodium hydride; lithium hydride; etc.), an additive (tetra-n-butylammonium iodide, potassium iodide, sodium iodide, etc.), which is advantageous.

A reaction solvent, which can be used, includes a solvent inert to this reaction, such as tetrahydrofuran, dichloromethane, dichloroethane, acetonitrile, dimethylformamide, dimethylsulfoxide, etc.

Process 5:

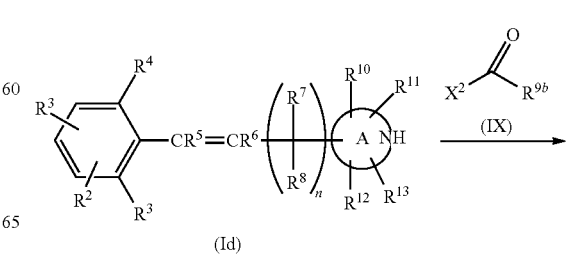

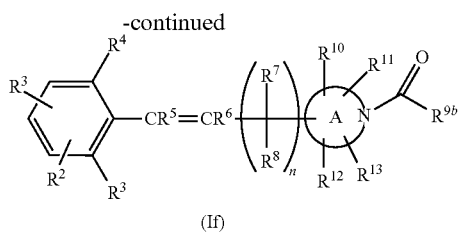

(If)

(wherein $R^{9b}$—CO— represents an optionally substituted an acyl; and $X^2$ represents OH; a leaving group such as a halogen, 1-hydroxybenzotriazol-1-yloxy, methoxy, phenoxy, azido, etc., or a leaving site in a mixed anhydride or a symmetric anhydride; hereinafter the same.)

This process is amidation. Specifically, the amidation is carried out as in the processes described above, e.g., by reacting an amine (Id) with a carboxylic acid or its reactive derivative (IX) in a chemically equivalent amount in accordance with the processes described in, e.g., M. Bodanszky, "Peptide Chemistry" (1988, pages 55-73), Nobuo Izumiya, et. al, "Basis and Experimentals of Peptide Synthesis" (1985, pages 89-142), etc.

Specifically, this reaction is preferably carried out by the method using a condensing agent conventionally used (dicyclohexylcarbodiimide, 1-ethyl-3-(3-dimethylaminopropyl) carbodiimide, 1,1'-carbonyldiimidazole (CDI), etc.); the mixed anhydride method using ethyl chloroformate or isobutyl chloroformate; the symmetric anhydride method using ethoxyacetylene, an alkynylamine such as tert-butylethynyldimethylamine, etc. If desired, a catalyst such as 1-hydroxybenzotriazole, etc. may be used. The reaction may also be carried out by reacting a carboxylic acid with a halogenating agent such as thionyl chloride, oxalyl chloride, phosphorus oxychloride, etc. to convert the acid into a reactive derivative such as an acid halide and then reacting the reactive derivative with a primary or secondary amine. The reaction is carried out in a solvent inert to this reaction such as tetrahydrofuran, dioxane, dichloromethane, dichloroethane, dimethylformamide, dimethylsulfoxide, toluene, etc., if necessary, in the presence of a base (e.g., an organic base such as triethylamine, diisopropylethylamine, pyridine, etc.; an inorganic base such as potassium carbonate, sodium hydrogencarbonate, etc.), under the conditions of ice cooling to heating with stirring.

Process 6:

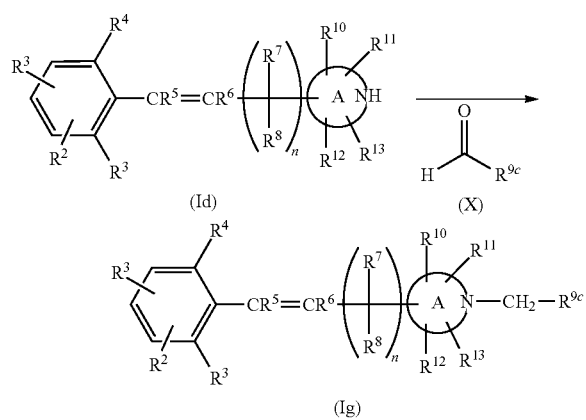

(wherein $R^{9c}$ represents a group having a carbon number less than by one from the optionally substituted lower alkyl shown by $R^9$, hereinafter the same).

This process is reductive amination.

Specifically, the reaction is carried out as in the processes described above, e.g., by reacting an amine (Id) with an aldehyde or ketone (X) in a conventional manner of reductive amination, e.g., the process described in "Experimental Chemistry Series (Maruzen)" (4th edition, 20, 1992, page 300), edited by The Chemical Society of Japan, etc.

Specifically, Compound (Ig) can be produced by reacting the amine with its chemically equivalent amount of the aldehyde or ketone in a solvent inert to this reaction such as tetrahydrofuran, dioxane, dichloromethane, dichloroethane, dimethylformamide, dimethylsulfoxide, toluene, etc., in the presence of a reducing agent such as sodium cyanoborohydride, sodium triacetoxyborohydride, sodium borohydride, formic acid, etc., under the conditions of ice cooling to heating with stirring. In some occasions, the reaction is carried out smoothly in the presence of an acid (e.g., a Lewis acid such as titanium tetraisopropoxide, etc.; acetic acid; p-toluenesulfonic acid, etc.), which is advantageous. The reduction described above may also be performed in the above-described solvent inert to the reaction by catalytic reduction in the presence of a metal catalyst such as palladium (Pd), platinum (Pt), etc.

The reducing agent may be added immediately after mixing the primary or secondary amine with the aldehyde or ketone or after passage of some time.

The foregoing shows the processes for producing representative compounds. In addition, compounds other than the compounds of the present invention or raw compounds but having similar substituents can be subjected to reactions for modifying substituents according to the processes described above to produce the compounds of the present invention. In addition to the processes described above, these compounds can be produced by other well known processes, including conventional imidation or amidination, or by the processes described in "Experimental Chemistry Series (Maruzen)" (4th edition, 25, pages 396-427) edited by The Chemical Society of Japan, Protective Group Organic Synthesis, Second Ed., John Wiley & Sons, Inc., or Angew. Chem. Int. Ed. Engl. 1998, 37, p 2046-2067, etc.

Compound (I) of the present invention thus produced is isolated in its free form or as its salt. The salt of Compound (I) of the present invention can be prepared by applying a conventional salt-making technique to Compound (I) of the present invention as the free base.

Also, Compound (I) of the present invention or its salt may be isolated and purified in the form of a hydrate, solvate or polymorphism thereof. The isolation and purification are performed by applying conventional chemical operations including extraction, concentration, distillation, crystallization, filtration, recrystallization, various chromatography techniques, etc.

Various isomers can be separated by choosing an appropriate raw compound, or by utilizing a difference between isomers in physical or chemical properties. For example, the optical isomers can be converted into stereochemically pure isomers, by choosing appropriate raw compounds or by racemic resolution of racemic compounds (for example, by a process of optical resolution which comprises converting the racemic compounds into diastereomer salts with ordinary optically active acids, etc.).

[Formulation]

Various formulations conventionally used are applicable to Compound (I) of the present invention. Representative formulations are explained below.

A pharmaceutical composition may contain one or two or more types of the Compound (I) of the present invention or pharmaceutically acceptable salts thereof as the effective ingredient and pharmaceutically acceptable carriers, which can be prepared into tablets, powders, fine granules, granules, capsules, pills, liquids, injections, suppositories, ointments, paps or the like, using carriers and excipients conventionally used to make pharmaceutical preparations, and other additives. The resulting formulations are administered orally (including sublingual administration) or parenterally.

The clinical dose of Compound (I) of the present invention or pharmaceutically acceptable salts to human is appropriately determined, depending on the symptom, age, sex and body weight of an individual patient, to whom Compound (I) or pharmaceutically acceptable salts is applied. Generally, Compound (I) or pharmaceutically acceptable salts is orally administered to an adult at a dose of 1 mg to 1000 mg per day in one portion or divided portions in the form of a solid composition or a liquid composition. Alternatively, the compound is intravenously administered to an adult at a dose of 1 mg to 500 mg per day in one portion or divided portions, or intravenously administered in a sustained release manner for a period of 1 hour to 24 hours per day. As described above, since the dose may vary depending upon various conditions and thus, a dose below the range given above may be sometimes sufficient.

As the solid composition for oral administration in accordance with the present invention, tablets, powders, granules and the like are used. For such solid composition, one or more active substances are mixed with at least one inactive diluent, for example lactose, mannitol, glucose, hydroxypropylcellulose, microcrystalline cellulose, starch, polyvinylpyrrolidone, or metasilicate aluminate magnesium. Following a conventional manner, the composition may further contain additives other than inactive diluents, for example, lubricants such as magnesium stearate, disintegrators such as cellulose calcium glycolate, stabilizers such as lactose, solubilization or dissolution-auxiliary agents such as glutamic acid or aspartic acid. The tablets or pills may be sugar-coated or coated with a gastric soluble or enteric film, using sucrose, gelatin, hydroxypropyl cellulose and hydroxypropylmethyl cellulose phthalate, and the like.

The liquid composition for oral administration contains pharmaceutically acceptable emulsifiers, solubilizers, suspending agents, syrups, elixirs and the like and also contains inactive diluents conventionally used, for example, distilled water or ethyl alcohol. The composition may further contain auxiliary agents such as solubilization- or dissolution-auxiliary agents, moisturizers and suspending agents, sweeteners, flavoring agents, aromatic agents and preservatives.

The injections for parenteral administration include aseptic, aqueous or non-aqueous solubilizers, suspending agents and emulsifiers. Aqueous solubilizers and suspending agents include, for example, distilled water for injections and physiological saline. Water-insoluble solubilizers and suspending agents include, for example, propylene glycol, polyethylene glycol, vegetable oils such as olive oil, alcohols such as ethanol, polysorbate 80 (trade name), etc. Such composition may further contain additives including isotonic agents, preservatives, moisturizers, emulsifiers, dispersants, stabilizers (for example, lactose), and solubilization- and dissolution-auxiliary agents. These are sterilized by filtration through, e.g., a bacteria retention filter, or by blending with sterilizers or irradiation. These may also be prepared into aseptic solid compositions and the resulting aseptic compositions are provided for use after dissolution in aseptic water or in an aseptic solvent for injections, prior to use.

Furthermore, Compound (I) of the present invention may be used in combination with therapeutics for the diseases described above or with other drugs useful for pain by a mechanism other than the sodium channel blockage. Drugs useful for pain, which are usable in combination, include narcotic analgesics, antipyretic analgesics, non-steroidal antiinflammatory drugs, etc.

EXAMPLES

Next, the present invention is described in more detail by referring to Examples but is not deemed to be limited thereto. Raw compounds used will be explained in Reference Examples.

The chemical structures of individual compounds obtained in Examples, Example Nos. using the compounds and specific constructions are shown in Tables 1 through 13 and the physicochemical properties of these compounds are shown in Tables 14 through 25 below.

Production examples of the raw compounds used in Examples are specifically described by referring to Reference Examples 1 through 33. The chemical structures of the compounds obtained in Reference Examples 4 to 15, 17, 22 to 25, 28 to 29 and 31 to 32 are shown in Table 26 and the physicochemical properties of the compounds of Reference Examples 1 through 33 are shown in Table 27.

Tables 1 to 25 relating to Examples and Tables 26 and 27 relating to Reference Examples are shown at the end of the specification.

The symbols in Tables 1 to 25 relating to Examples and Tables 26 and 27 relating to Reference Examples are used to mean the following.

Rf.: Reference Example No., Ex.: Example No., Me: methyl, Et: ethyl, Pr: propyl, iPr: isopropyl, Bu: butyl, iBu: isobutyl, tBu: tert-butyl, Ph: phenyl, Ac: acetyl, Bn: benzyl, cBu: cyclobutyl, cPen: cyclopentyl, cHex: cyclohexyl, cHep: cycloheptyl, Mo: morpholine, ThioMo: thiomorpholine, Py: pyridine, Pyrrolid: pyrrolidine, Piperi: piperidine, Pipera: piperazine, IM: imidazole, MeO: methoxy, EtO: ethoxy, $Me_2N$: dimethylamino, PhO: phenoxy, $Bu_2N$: dibutylamino, yl: yl, Salt: salt, fum: fumarate, difumarate: difumarate, dimaleate: dimaleate, Structure: structural formula, NMR: nuclear magnetic resonance spectrum (unless otherwise indicated, 400 MHz, DMSO-$d_6$, TMS internal standard, δ ppm), MS: mass spectrum (unless otherwise indicated, FAB or ESIm/z), Data: physicochemical property.

Reference Example 1

1) 3.32 g of aniline was added to a solution of 4.99 g of 2-chlorobenzaldehyde in 48 ml of benzene, and the mixture was heated under reflux for 20 hours. After the reaction mixture was concentrated under reduced pressure, the concentrate was azeotropically distilled with toluene to give 6.16 g of yellow oil. The yellow oil was dissolved in 120 ml of acetic acid and 5.45 g of palladium acetate was added to the solution, followed by heating under reflux for 2 hours. After cooling, water was added to the reaction mixture and the precipitated crystals were collected by filtration. The crystals were dissolved in 50 ml of methylene chloride, and 75 ml of saturated aqueous sodium chloride and 50 ml of acetone were added to the solution. The mixture was stirred at ambient temperature for 15 hours. The precipitated crystals were collected by filtration and washed with ethanol, benzene and methylene chloride to give 5.50 g of green crystals. The crystals were suspended in 250 ml of benzene and 8.08 g of triphenylphosphine was added to the suspension, followed by stirring at ambient temperature for 50 minutes. To the reaction mixture was added 13 ml of 1.2M methyl lithium in diethyl ether. The mixture was stirred for 2 hours and 250 ml of 1N hydrochloric acid was further added thereto, followed by stirring for 2 hours. The reaction mixture was extracted with diethyl ether. The organic layer was washed with saturated aqueous sodium chloride and then dried over anhydrous sodium sulfate. After filtration, the filtrate was concentrated and the resulting residue was purified by silica gel column chromatography (hexane-ethyl acetate) to give 1.51 g of 2-chloro-6-methylbenzaldehyde as pale yellow oil.

2) Under ice cooling, 185 mg of sodium borohydride was added to a solution of 1.51 g of 2-chloro-6-methylbenzaldehyde in 15 ml of methanol, followed by stirring for 35 minutes. The reaction mixture was concentrated under reduced pressure and saturated aqueous ammonium chloride was added to the residue. The mixture was extracted with diethyl ether. The organic layer was washed with saturated aqueous sodium chloride and then dried over anhydrous sodium sulfate. After filtration, the filtrate was concentrated and the resulting residue was purified by silica gel column chromatography (hexane-ethyl acetate) to give 1.24 g of 2-chloro-6-methylbenzyl alcohol as colorless crystals.

3) Under ice cooling, 5 drops of dimethylformamide and 0.75 ml of thionyl chloride were added to a solution of 1.24 g of 2-chloro-6-methylbenzyl alcohol in 15 ml of toluene. The mixture was stirred at ambient temperature for 2 hours. The reaction mixture was concentrated under reduced pressure and the residue was then azeotropically distilled with 5 ml of toluene 3 times to give an oil. The resulting oil was dissolved in 15 ml of acetonitrile, and 2.08 g of triphenylphosphine was added to the solution. The mixture was heated under reflux for 16 hours. The reaction mixture was concentrated under reduced pressure and the collected crystals were washed with ethyl acetate to give 3.15 g of (2-chloro-6-methylbenzyl)(triphenyl)phosphonium chloride as colorless crystals.

Reference Example 2

After 250 ml of water, 60 ml of ethanol, 18.3 g of phenyl boronic acid, 39.8 g of sodium carbonate and 1.1 g of palladium chloride were added to a solution of 20.0 g of 4-bromo-2,6-dimethylaniline in 250 ml of toluene, the mixture was heated under reflux for 18.5 hours. After cooling, the organic layer was fractionated and the aqueous layer was extracted with toluene. The combined organic layer was washed with saturated aqueous sodium chloride and then dried over anhydrous sodium sulfate. The solvent was then evaporated under reduced pressure. The residue was purified by silica gel column chromatography (hexane-ethyl acetate) to give 18.5 g of brown oil. The oil was suspended in 45 ml of 48% hydrobromic acid and 125 ml of water, and 100 ml of an aqueous solution of 7.11 g of sodium sulfite was dropwise added to the suspension under ice cooling. After 0.31 g of copper powder was added thereto, the mixture was heated under reflux for 2 hours. The mixture was allowed to cool and then extracted with toluene. The organic layer was washed with 50% aqueous sodium hydroxide solution and saturated aqueous sodium chloride and then dried over anhydrous sodium sulfate. The solvent was evaporated under reduced pressure. The resulting residue was purified by silica gel column chromatography (hexane-ethyl acetate) to give 5.69 g of 4-bromo-3,5-dimethylbiphenyl.

Reference Example 3

To a solution of 12.0 g of 4-bromo-3,5-dimethylphenol in 300 ml of methylene chloride was added 21.7 g of phenyl boronic acid, 32.5 g of copper acetate, 126 ml of triethylamine and 36.0 g of molecular sieves (4A), and the mixture was heated under reflux for 47 hours. The reaction mixture was filtered and the filtrate was concentrated under reduced pressure. The residue was purified by silica gel column chromatography (hexane) to give 5.23 g of colorless oil. Grignard reagent was prepared from the oil, 0.51 g of magnesium and 25 ml of tetrahydrofuran. Under ice cooling, a solution of 1.27 g of dimethylformamide in 15 ml of tetrahydrofuran was added dropwise to the reagent. After stirring at ambient temperature for 45 minutes, the reaction mixture was poured into saturated aqueous ammonium chloride, followed by extraction with diethyl ether. The organic layer was washed with saturated aqueous sodium chloride and then dried over anyhydrous sodium sulfate and the solvent was evaporated under reduced pressure. The resulting residue was purified by silica gel column chromatography (hexane-ethyl acetate) to give 3.79 g of pale yellow oil. This oil was dissolved in 40 ml of methanol. Under ice cooling, 0.32 g of sodium borohydride was added to the solution, followed by stirring at ambient temperature for 45 minutes. The reaction mixture was concentrated under reduced pressure and saturated aqueous ammonium chloride solution was added to the residue, followed by extraction with ethyl acetate. The organic layer was washed with saturated aqueous sodium chloride and then dried over anhydrous sodium sulfate. The solvent was evaporated under reduced pressure to give 3.78 g of (2,6-dimethyl-4-phenoxyphenyl)methanol.

The compound of Reference Example 4 was obtained in a manner similar to Reference Example 3.

The compounds of Reference Example 5 to 15 were obtained in a manner similar to Reference Example 1.

Reference Example 16

After 4.34 g of N-bromosuccinimide and 0.54 g of benzoyl peroxide were added to a solution of 3.03 g of 2,3-dimethylanisole in 70 ml of carbon tetrachloride, the mixture was heated under reflux for 30 minutes. After cooling, insoluble solid in the reaction mixture were filtered off and the filtrate was concentrated under reduced pressure to give an oil. The obtained oil was dissolved in 50 ml of benzene, and 5.82 g of triphenylphosphine was added to the solution. The mixture was heated under reflux for 11 hours. After cooling, the precipitated crystals were collected by filtration and recrystallized from methylene chloride-benzene to give 6.51 g of (2-methoxy-6-methylbenzyl)(triphenyl)phosphonium bromide as colorless crystals.

The compound of Reference Example 17 was obtained in a manner similar to Reference Example 16.

Reference Example 18

After 10.4 g of potassium carbonate and 6.80 ml of methyl iodide were added to a solution of 10.0 g of 4-bromo-3,5-dimethylphenol in 100 ml of acetone, the mixture was heated under reflux for 15 hours. The reaction mixture was concentrated under reduced pressure and saturated aqueous ammonium chloride was added to the residue, followed by extraction with ethyl acetate. The organic layer was washed with saturated aqueous sodium chloride and then dried over anhydrous sodium sulfate. After filtration, the filtrate was concentrated and the resulting residue was purified by silica gel column chromatography (hexane-ethyl acetate) to give 9.18 g of 4-bromo-3,5-dimethylanisole as colorless oil.

Reference Example 19

Ethyl 4-(hydroxyimino)cyclohexanecarboxylate was reacted in the presence of conc. sulfuric acid in ethanol to produce ethyl 7-oxoazepane-4-carboxylate.

Reference Example 20

Ethyl 7-oxoazepane-4-carboxylate was reacted in the presence of lithium aluminum hydride to produce azepan-4-yl-methanol.

Reference Example 21

8.60 ml of di-tert-butyl dicarbonate was added to a solution of 5.00 g of 2-piperidin-4-ylethanol in 50 ml of tetrahydrofuran, followed by stirring at ambient temperature for 30 minutes. The reaction mixture was concentrated under reduced pressure and the resulting residue was purified by silica gel column chromatography (hexane-ethyl acetate) to give 8.80 g of an oil. The oil was dissolved in 60 ml of dimethylsulfoxide, and the resulting solution was added 20.5 ml of triethylamine and 12.2 g of sulfur trioxide-pyridine complex, followed by stirring at ambient temperature for 30 minutes. The reaction mixture was poured into saturated aqueous sodium bicarbonate, followed by extraction with ethyl acetate. The organic layer was washed with saturated aqueous sodium chloride and then dried over anhydrous sodium sulfate. After filtration, the filtrate was concentrated and the residue was purified by silica gel column chromatography (hexane-ethyl acetate) to give 6.40 g of tert-butyl 4-(2-oxoethyl)piperidine-1-carboxylate.

The compounds of Reference Examples 22 to 25 were produced in a manner similar to Reference Example 21.

Reference Example 26

(1-Benzylpyrolidin-3-yl)methanol was reacted in the presence of triethylamine and sulfur trioxide-pyridine complex in dimethylsulfoxide to produce 1-benzylpyrrolidine-3-carbaldehyde.

Reference Example 27 tert-Butyl 3-oxo-8-azabicyclo[3.2.1]octane-8-carboxylate was reacted in the presence of p-toluenesulfonylmethylisocyanide, potassium tert-butoxide and ethanol in 1,2-dimethoxyethane to produce tert-butyl 3-cyano-8-azabicyclo[3.2.1]octane-8-carboxylate.

The compounds of Reference Examples 28 to 29 were produced in a manner similar to Reference Example 27.

Reference Example 30 tert-Butyl 3-cyano-8-azabicyclo[3.2.1]octane-8-carboxylate was reacted in the presence of diisobutyl aluminum hydride in tetrahydrofuran to produce tert-butyl 3-formyl-8-azabicyclo[3.2.1]octane-8-carboxylate.

The compounds of Reference Examples 31 to 32 were produced in a manner similar to Reference Example 30.

Reference Example 33

Under ice cooling, 18 ml of 2-(bromomethyl)-1,3-dioxolane, 9.87 g of potassium tert-butoxide and 6.57 g of tetrabutylammonium iodide were added to a solution of 14.0 g of methyl 2-oxopiperidine-4-carboxylate in 300 ml of tetrahydrofuran and 50 ml of dimethylformamide, and the mixture was stirred at 70° C. for 14 hours. The reaction mixture was poured into water, followed by extraction with ethyl acetate. The organic layer was washed with saturated aqueous sodium chloride and then dried over anhydrous sodium sulfate. After filtration, the filtrate was concentrated and the resulting residue was purified by silica gel column chromatography (hexane-ethyl acetate) to give 4.50 g of yellow oil. This oil was dissolved in 90 ml of tetrahydrofuran and 1.00 g of lithium borohydride was added to the solution under ice cooling, followed by stirring at ambient temperature for 4 hours. After saturated aqueous ammonium chloride solution was added to the reaction mixture, the mixture was extracted with chloroform. The organic layer was washed with saturated aqueous sodium chloride and then dried over anhydrous sodium sulfate. After filtration, the filtrate was concentrated and the resulting residue was purified by silica gel column chromatography (chloroform-methanol) to give 2.60 g of colorless oil. This oil was dissolved in 30 ml of dimethylsulfoxide, and 5.14 g of triethylamine and 4.04 g of sulfur trioxide-pyridine complex were added to the solution, followed by stirring at ambient temperature for 1.5 hour. The reaction mixture was poured into water, followed by extraction with chloroform. The organic layer was washed with saturated aqueous sodium chloride and then dried over anhydrous sodium sulfate. The solvent was evaporated under reduced pressure to give 2.36 g of 1-(1,3-dioxolan-2-ylmethyl)-2-oxopiperidine-4-carbaldehyde.

Example 1

264 mg of sodium hydride (55%) was added to a solution of 2.65 g of (2-chloro-6-methylbenzyl)(triphenyl)phosphonium chloride in 20 ml of dimethylsulfoxide, followed by stirring at ambient temperature for 1 hour. After 994 mg of tert-butyl 4-formylpiperidine-1-carboxylate was added to the reaction mixture, the mixture was stirred at ambient temperature for 1 hour. The reaction mixture was poured into saturated aqueous ammonium chloride, followed by extraction with ethyl acetate. The organic layer was washed with water and saturated aqueous sodium chloride and then dried over anhydrous sodium sulfate. After filtration, the filtrate was concentrated and the resulting residue was purified by silica gel column chromatography (hexane-ethyl acetate) to give 645 mg of tert-butyl 4-[(E)-2-(2-chloro-6-methylphenyl)vinyl]piperidine-1-carboxylate as an oil.

Example 2

As starting materials, 5.00 g of (2,6-dimethylbenzyl)(triphenyl)phosphonium chloride and 1.79 g of tert-butyl 4-formylpiperidine-1-carboxylate were used and treated in the same manner as in Example 1. The reaction mixture was then purified by silica gel column chromatography (hexane-ethyl acetate) to give 192 mg of tert-butyl 4-[(Z)-2-(2,6-dimethylphenyl)vinyl]piperidine-1-carboxylate (Example 2-1) and 1.96 g of tert-butyl 4-[(E)-2-(2,6-dimethylphenyl)vinyl]piperidine-1-carboxylate (Example 2-2).

The compounds of Examples 3 to 14, 16 to 24, 27 and 28 were produced in a manner similar to Example 1.

The compounds of Examples 15-1, 15-2, 25-1, 25-2, 26-1 and 26-2 were produced in a manner similar to Example 2.

Example 29

Under argon atmosphere, 1M tetrahydrofuran solution of 1.3 ml of lithium bis(trimethylsilyl)amide was added at −78° C. to a solution of 300 mg of tert-butyl 4-acetylpiperidine-1-carboxylate in 4.0 ml of tetrahydrofuran, followed by stirring for 15 minutes. To the reaction mixture, a solution of 167 mg of 2,6-dimethylbenzaldehyde in 1.0 ml of tetrahydrofuran was added, followed by stirring at ambient temperature for 12 hours. Saturated aqueous ammonium chloride solution was added to the reaction mixture, followed by extraction with diethyl ether. The organic layer was washed with water and then dried over anhydrous sodium sulfate. After filtration, the filtrate was concentrated and the residue was purified by silica gel column chromatography (hexane-ethyl acetate) to give 235 mg of tert-butyl 4-[(E)-3-(2,6-dimethylphenyl)prop-2-enoyl]piperidine-1-carboxylate.

Example 30

Under cooling at −78° C., a solution of 1.50 g of 4-bromo-2,6-dimethylanisole in 20 ml of tetrahydrofuran was added to a solution of 1.6M hexane solution of 4.8 ml of n-butyl lithium in 20 ml of tetrahydrofuran. The mixture was stirred for 1 hour. A solution of 1.50 g of tert-butyl 4-(2-oxoethyl)piperidine-1-carboxylate in 20 ml of tetrahydrofuran was added to the mixture. After stirring for 30 minutes, the mixture was stirred at ambient temperature for further 3 hours. The reaction mixture was poured into water, followed by extraction with ethyl acetate. The organic layer was washed with saturated aqueous sodium chloride and then dried over anhydrous sodium sulfate. After filtration, the filtrate was concentrated and the resulting residue was purified by silica gel column chromatography (hexane-ethyl acetate) to give 628 mg of tert-butyl 4-[2-hydroxy-2-(4-methoxy-2,6-dimethylphenyl)ethyl]piperidine-1-carboxylate as an oil. To the oil was added 15 ml of 10% hydrochloric acid and the mixture was heated under reflux for 2 hours. After cooling, the reaction mixture was alkalized with 20% aqueous sodium hydroxide solution, followed by extraction with ethyl acetate. The organic layer was washed with saturated aqueous sodium chloride and then dried over anhydrous magnesium sulfate. The solvent was evaporated under reduced pressure to give 291 mg of tert-butyl 4-[(E)-2-(4-methoxy-2,6-dimethylphenyl)vinyl]piperidine-1-carboxylate.

Example 31

Under argon atmosphere, 3 ml of propionitrile was added to a mixture of 339 mg of tert-butyl 4-[(E)-2-(4-bromo-2,6-dimethylphenyl)vinyl]piperidine-1-carboxylate, 89 mg of sodium cyanide, 53 mg of tetrakistriphenylphosphine palladium and 17 mg of copper iodide, followed by heating under reflux for 7 hours. Water was added to the reaction mixture, followed by extraction with ethyl acetate. The extract was dried over anhydrous magnesium sulfate and the residue was purified by silica gel column chromatography (hexane-ethyl acetate) to give 299 mg of tert-butyl 4-[(E)-2-(4-cyano-2,6-dimethylphenyl)vinyl]piperidine-1-carboxylate.

Example 32

Under carbon monoxide atmosphere, 120 μl of butanol and 265 μl of tributylamine were added to a mixture of 409 mg of tert-butyl 4-[(E)-2-(4-bromo-2,6-dimethylphenyl)vinyl]piperidine-1-carboxylate and 39 mg of dichlorobistriphenylphosphine palladium. The mixture was heated at 100° C. overnight with stirring. Then 87 mg of dichlorobistriphenylphosphine palladium, 120 μl of butanol and 265 μl of tributylamine were added to the reaction mixture and the mixture was heated at 120° C. overnight with stirring. Water was added to the reaction mixture, followed by extraction with ethyl acetate. The organic layer was washed sequentially with 0.1N hydrochloric acid, saturated aqueous sodium hydrogen carbonate solution, water and saturated aqueous sodium chloride. After drying over anhydrous magnesium sulfate, the solvent was evaporated under reduced pressure. The residue was purified by silica gel column chromatography (hexane-ethyl acetate) to give 217 mg of tert-butyl 4-{(E)-2-[4-(butoxycarbonyl)-2,6-dimethylphenyl]vinyl}piperidine-1-carboxylate (Example 32-1) and 123 mg of tert-butyl 4-((E)-2-{4-[(dibutylamino)carbonyl]-2,6-dimethylphenyl}vinyl)piperidine-1-carboxylate (Example 32-2).

Example 33

Under argon atmosphere, 10 ml of toluene and 87 μl of morpholine were added to a mixture of 300 mg of tert-butyl 4-[(E)-2-(4-bromo-2,6-dimethylphenyl)vinyl]piperidine-1-carboxylate, 110 mg of sodium tert-butoxide, 45 mg of bis-dibenzylideneacetone palladium and 48 mg of BINAP. The resulting mixture was heated at 100° C. for 11 hours with stirring. The solvent was evaporated under reduced pressure and the residue was purified by silica gel column chromatography (hexane-ethyl acetate) to give 289 mg of tert-butyl 4-[(E)-2-(2,6-dimethylphenyl-4-morpholin-4-yl-phenyl)vinyl]piperidine-1-carboxylate.

The compound of Example 34 was produced in a manner similar to Example 33.

Example 35

To a suspension of 133 mg of tert-butyl 4-[(E)-2-(4-cyano-2,6-dimethylphenyl)vinyl]piperidine-1-carboxylate in 5 ml of acetone and 2 ml of water, 146 mg of hydrogen peroxide-urea complex and 7 mg of potassium carbonate were added, followed by stirring overnight. Then, 221 mg of hydrogen peroxide-urea complex was added and the mixture was stirred overnight, and 293 mg of hydrogen peroxide-urea complex was further added, followed by stirring for 4 days. An aqueous solution of sodium sulfate was added to the reaction mixture and extracted with chloroform. The organic layer was washed with saturated aqueous sodium chloride and then dried over anhydrous magnesium sulfate. The solvent was evaporated under reduced pressure and the residue was purified by silica gel column chromatography (chloroform-methanol) to give 134 mg of tert-butyl 4-{(E)-2-[4-(aminocarbonyl)-2,6-dimethylphenyl]vinyl}piperidine-1-carboxylate.

Example 36

To a solution of 209 mg of tert-butyl 4-{(E)-2-[4-(butoxycarbonyl)-2,6-dimethylphenyl]vinyl}piperidine-1-carboxylate in 5 ml of ethanol, 1.5 ml of 1N aqueous sodium hydroxide solution was added, followed by stirring at ambient temperature for 3.5 hours. After 1 ml of tetrahydrofuran was added to the reaction mixture, the mixture was stirred at 50° C. overnight. The solvent was evaporated under reduced pressure, water and 1.6 ml of 1N hydrochloric acid were added

Example 37

To a solution of 645 mg of tert-butyl 4-[(E)-2-(2-chloro-6-methylphenyl)vinyl]piperidine-1-carboxylate in 4 ml of ethanol, 3 ml of 35% hydrogen chloride-ethanol was added, followed by stirring at ambient temperature for 5 hours. The reaction mixture was evaporated under reduced pressure and the residue was azeotropically distilled with 5 ml of toluene 3 times to give crystals. The collected crystals were recrystalized from ethanol-ethyl acetate to give 377 mg of 4-[(E)-2-(2-chloro-6-methylphenyl)vinyl]piperidine hydrochloride.

The compounds of Examples 38 to 67 were produced in a manner similar to Example 37.

Example 68

To a solution of 125 mg of 1-benzyl-4-[(E)-2-(2,6-dimethylphenyl)vinyl]-3-methylpiperidine in 3 ml of 1,2-dichloroethane, 139 mg of 1-chloroethyl chloroformate was added at ambient temperature. The mixture was heated under reflux for 1 hour. After cooling, 10 ml of methanol was added to the reaction mixture and the resulting mixture was heated under reflux for further 30 minutes. After cooling, the solvent was evaporated under reduced pressure. The residue was dissolved in 5 ml of ethyl acetate and the solution was filtered. To the filtrate was added 1 ml of 4N hydrochloric acid-ethyl acetate and the solvent was evaporated under reduced pressure. The residue was triturated in ethyl acetate. After filtration, the obtained solid was recrystallized from ethyl acetate-methanol to give 47 mg of 4-[(E)-2-(2,6-dimethylphenyl)vinyl]-3-methylpiperidine hydrochloride.

The compound of Example 69 was produced in a manner similar to Example 68.

Example 70

To a solution of 520 mg of 2-[(E)-2-(2,6-dimethylphenyl)vinyl]piperidine monohydrochloride in 7 ml of dimethylformamide, 0.13 ml of methyl iodide, 0.58 ml of triethylamine and 572 mg of potassium carbonate were added, followed by stirring at ambient temperature for 12 hours. The reaction mixture was poured into water, followed by extraction with ethyl acetate. The organic layer was washed with saturated aqueous sodium chloride and then dried over anhydrous sodium sulfate. After filtration, the filtrate was concentrated and the resulting residue was purified by silica gel column chromatography (chloroform-methanol) to give 470 mg of 2-[(E)-2-(2,6-dimethylphenyl)vinyl]-1-methylpiperidine.
The product was dissolved in 5 ml of ethanol, and 2.5 ml of 35% hydrogen chloride-ethanol was added to the solution, followed by stirring at ambient temperature for 1 hour. The reaction mixture was evaporated under reduced pressure and the residue was azeotropically distilled with 5 ml of toluene 3 times to give crystals. The collected crystals were recrystalized from ethanol-ethyl acetate to give 395 mg of 2-[(E)-2-(2,6-dimethylphenyl)vinyl]-1-methylpiperidine monohydrochloride.

The compounds of Examples 71 to 77 were produced in a manner similar to Example 70.

Example 78

Under ice cooling, 6.77 ml of triethylamine and 3.87 ml of chloroacetyl chloride were added to a solution of 9.96 g of 4-[(E)-2-(2,6-dimethylphenyl)vinyl]piperidine in 150 ml of tetrahydrofuran. After stirring at ambient temperature for 20 minutes, 200 ml of water was added to the mixture. After the organic layer was fractionated, the aqueous layer was extracted with diethyl ether. The combined organic layer was and washed with saturated aqueous sodium chloride. After drying over anhydrous magnesium sulfate, the solvent was evaporated under reduced pressure. The residue was purified by silica gel column chromatography (hexane-ethyl acetate). The collected crystals were washed with diisopropyl ether-hexane and dried under reduced pressure to give 10.69 g of 1-(chloroacetyl)-4-[(E)-2-(2,6-dimethylphenyl)vinyl]piperidine.

The compounds of Examples 79 to 84 were produced in a manner similar to Example 78.

Example 85

To a solution of 200 mg of 4-[(E)-2-(2,6-dimethylphenyl)vinyl]piperidine monohydrochloride in 5 ml of dimethylformamide, 111 µl of triethylamine, 107 mg of imidazole-4-carboxylic acid, 161 mg of 1-hydroxybenzotriazole and 228 mg of 1-ethyl-3-(3-dimethylaminopropyl)carbodiimide hydrochloride were added at ambient temperature. After stirring at ambient temperature overnight, the reaction mixture was concentrated under reduced pressure. After 50 ml of chloroform and 15 ml of saturated aqueous sodium hydrogen carbonate solution were added to the reaction mixture, the organic layer was fractionated and the solvent was evaporated under reduced pressure. The residue was purified by silica gel column chromatography (chloroform-methanol-ammonia water) to give 280 mg of colorless oil. The oil obtained was dissolved in 2 ml of ethanol, and 226 µl of 4N hydrochloric acid-ethyl acetate was added to the solution. The precipitated crystals were collected by filtration and washed with diethyl ether. The crystals were recrystallized from ethanol-diethyl ether to give 191 mg of 4-[(E)-2-(2,6-dimethylphenyl)vinyl]-1-(1H-imidazol-4-ylcarbonyl)piperidine monohydrochloride.

The compounds of Examples 86 to 107 were produced in a manner similar to Example 85.

Example 108

To a solution of 250 mg of 4-[(E)-2-(2,6-dimethylphenyl)vinyl]piperidine monohydrochloride in 5 ml of dimethylformamide, 138 µl of triethylamine, 222 mg of 2-[(tert-butoxycarbonyl)amino]-2-methylpropionic acid, 201 mg of 1-hydroxybenzotriazole and 286 mg of 1-ethyl-3-(3-dimethylaminopropyl)carbodiimide hydrochloride were added at ambient temperature. After stirring at ambient temperature overnight, the reaction mixture was concentrated under reduced pressure. After 50 ml of chloroform and 15 ml of saturated aqueous sodium hydrogencarbonate solution were added to the residue, the organic layer was fractionated and the solvent was evaporated under reduced pressure. The residue was purified by silica gel column chromatography (hexane-ethyl acetate) to give 364 mg of white crystals. The collected crystals were dissolved in 5 ml of 4N hydrochloric acid-ethyl acetate. After stirring at ambient temperature for 1 hour, 10 ml of diethyl ether was added to the solution, followed by stirring for 30 minutes. The precipitated crystals were collected by filtration and washed with diethyl ether. The crystals were recrystallized from ethanol-diethyl ether to give 227 mg of (2-{4-[(E)-2-(2,6-dimethylphenyl)vinyl]piperidin-1-yl}-1,1-dimethyl-2-oxoethyl)amine monohydrochloride.

The compounds of Examples 109 to 122 were produced in a manner similar to Example 108.

Example 123

To a solution of 300 mg of 4-[(E)-2-(2,6-dimethylphenyl)vinyl]piperidine monohydrochloride in 5 ml of ethanol, 736 mg of ethyl acetimidate hydrochloride and 996 μl of triethylamine were added at ambient temperature. After stirring at ambient temperature overnight, the reaction mixture was concentrated under reduced pressure. After 50 ml of chloroform and 15 ml of saturated aqueous sodium hydrogencarbonate solution were added to the reaction mixture, the organic layer was fractionated and the solvent was evaporated under reduced pressure. The residue was purified by silica gel column chromatography (chloroform-methanol-ammonia water) to give 313 mg of pale yellow crystals. The collected crystals were dissolved in 5 ml of ethanol, and 305 μl of 4N hydrochloric acid-ethyl acetate was added to the solution. The solvent was evaporated under reduced pressure. The residue was crystallized from ethanol-diethyl ether and the precipitated crystals were collected by filtration and washed with diethyl ether. The crystals were recrystallized from ethanol-diethyl ether to give 89 mg of 4-[(E)-2-(2,6-dimethylphenyl)vinyl]-1-(1-iminoethyl)piperidine monohydrochloride.

Example 124

349 mg of 1H-pyrazole-1-carboxamidine and 1.45 ml of N,N-diisopropylethylamine were added to a solution of 300 mg of 4-[(E)-2-(2,6-dimethylphenyl)vinyl]piperidine monohydrochloride in 5 ml of dimethylformamide at ambient temperature. After stirring at ambient temperature overnight, the reaction mixture was concentrated under reduced pressure. The residue was purified by silica gel column chromatography (ethyl acetate-ethanol-water) to give 427 mg of white crystals. The obtained crystals were dissolved in 5 ml of methanol, and 415 μl of 4N hydrochloric acid-ethyl acetate was added to the solution. The solvent was evaporated under reduced pressure and the residue was crystallized from ethanol-diethyl ether. The precipitated crystals were collected by filtration and washed with diethyl ether. The crystals were recrystallized from ethanol-diethyl ether to give 154 mg of 1-amidino-4-[(E)-2-(2,6-dimethylphenyl)vinyl]piperidine monohydrochloride.

Example 125

84 mg of 1H-imidazole and 142 mg of potassium carbonate were added to a solution of 300 mg of 1-(chloroacetyl)-4-[(E)-2-(2,6-dimethylphenyl)vinyl]piperidine in 5 ml of acetonitrile, followed by heating under reflux for 3 hours. After cooling, saturated aqueous sodium hydrogencarbonate solution was added to the reaction mixture, followed by extraction with chloroform. The organic layer was concentrated under reduced pressure and the residue was purified by silica gel column chromatography (chloroform-methanol-ammonia water) to give 314 mg of 4-[(E)-2-(2,6-dimethylphenyl)vinyl]-1-(1H-imidazol-1-ylacetyl)piperidine as yellow crystals. A portion of 288 mg from the crystals was dissolved in 2 ml of ethanol and 334 μl of 4N hydrochloric acid-ethyl acetate was added to the solution, followed by concentrating under reduced pressure. The residue was crystallized from ethanol-diethyl ether and the crystals were collected by filtration. The crystals were then washed with diethyl ether. The crystals were recrystallized from ethanol-diethyl ether to give 188 mg of 4-[(E)-2-(2,6-dimethylphenyl)vinyl]-1-(1H-imidazol-1-ylacetyl)piperidine monohydrochloride.

The compounds of Examples 126 to 196 were produced in a manner similar to Example 125.

Example 197

329 mg of tert-butyl (3S)-piperidin-3-ylcarbamate and 189 mg of potassium carbonate were added to a solution of 400 mg of 1-(chloroacetyl)-4-[(E)-2-(2,6-dimethylphenyl)vinyl]piperidine in 10 ml of acetonitrile, followed by heating under reflux for 2 hours. After the reaction mixture was concentrated under reduced pressure, chloroform and saturated aqueous sodium hydrogencarbonate solution were added to the residue, then the organic layer was fractionated. The solvent was evaporated under reduced pressure. The residue was purified by silica gel column chromatography (chloroform-methanol-ammonia water). The obtained oil was dissolved in 10 ml of ethanol, and 10 ml of 4N hydrochloric acid-ethyl acetate was added to the solution, followed by stirring at ambient temperature for 3 hours. The reaction mixture was concentrated under reduced pressure and the resulting residue was crystallized from 2-propanol-diisopropyl ether. The crystals were recrystallized from water-ethanol to give 473 mg of (3S)-1-(2-{4-[(E)-2-(2,6-dimethylphenyl)vinyl]piperidin-1-yl}-2-oxoethyl)piperidine-3-amine dihydrochloride.

The compounds of Examples 198 to 206 were produced in a manner similar to Example 197.

Example 207

454 μl of 37% aqueous formaldehyde solution and 175 μl of acetic acid were added to a solution of 219 mg of (2-{4-[(E)-2-(2,6-dimethylphenyl)vinyl]piperidin-1-yl}-2-oxoethyl)tetrahydro-2H-pyran-4-ylamine in 5 ml of dichloroethane, followed by stirring at ambient temperature for 2 hours. Subsequently, 388 mg of sodium triacetoxyborohydride was added to the reaction mixture, followed by stirring at ambient temperature for 1 hour. Saturated aqueous sodium hydrogencarbonate solution and chloroform were added to the mixture, then the organic layer was fractionated and the solvent was evaporated under reduced pressure. The residue was purified by silica gel column chromatography (chloroform-methanol-ammonia water). The resulting oil was dissolved in 5 ml of ethanol, and 172 μl of 4N hydrochloric acid-ethyl acetate was added to the mixture. The solvent was evaporated under reduced pressure. The residue was crystallized from 2-propanol-diisopropyl ether. The crystals were recrystallized from 2-propanol-diisopropyl ether to give 201 mg of (2-{4-[(E)-2-(2,6-dimethylphenyl)vinyl]piperidin-1-yl}-2-oxoethyl)methyl(tetrahydro-2H-pyran-4-yl)amine monohydrochloride.

The compounds of Examples 208 to 222 were produced in a manner similar to Example 207.

Example 223

A solution of 200 mg of 4-(2-{4-[(E)-2-(2,6-dimethylphenyl)vinyl]piperidin-1-yl}-2-oxoethyl)morpholine in 1 ml of tetrahydrofuran was added dropwise to a suspension of 42 mg of lithium aluminum hydride in 6 ml of tetrahydrofuran under ice cooling, followed by heating under reflux for 2 hours. The mixture was then allowed to cool. Under ice cooling, 42 μl of water, 42 μl of 15% aqueous sodium hydroxide solution and then 126 μl of water were sequentially added to the reaction mixture. After stirring at ambient temperature for 30 minutes, 500 mg of anhydrous sodium sulfate was added and insoluble solid was filtered. The filtrate was evaporated under reduced pressure and the residue was purified by silica gel column chromatography (chloroform-methanol-ammonia water) to give 150 mg of yellow oil. A portion of 143 mg from the oil was dissolved in 5 ml of ethyl acetate, and 2 ml of 4N hydrochloric acid-ethyl acetate was added to the solution. The solvent was evaporated under reduced pressure and the residue was washed with acetonitrile to give 133 mg of 4-(2-{4-[(E)-2-(2,6-dimethylphenyl)vinyl]piperidin-1-yl}ethyl)morpholine dihydrochloride.

The compound of Example 224 was produced in a manner similar to Example 223.

Example 225

675 µl of morpholine was added dropwise to a solution of 380 mg of 1-(acryloyl)-4-[(E)-2-(2,6-dimethylphenyl)vinyl]piperidine in 10 ml of toluene. The mixture was heated under reflux for 2 days in total. After the reaction mixture was concentrated under reduced pressure, the residue was purified by silica gel column chromatography (chloroform-methanol-ammonia water). The obtained oil was dissolved in 5 ml of ethanol, and 2 ml of 4N hydrochloric acid-ethyl acetate was added to the solution. The solvent was evaporated under reduced pressure. The precipitated crystals were recrystallized from ethanol to give 450 mg of 4-(3-{4-[(E)-2-(2,6-dimethylphenyl)vinyl]piperidin-1-yl}-3-oxopropyl)morpholine monohydrochloride.

Example 226

After 3 ml of 10% hydrochloric acid was added to a solution of 818 mg of 4-[(E)-2-(2,6-dimethylphenyl)vinyl]-1-(1,3-dioxolane-2-ylmethyl)piperidin-2-one in 10 ml of tetrahydrofuran, the mixture was heated under reflux for 4.5 hours. After cooling, the reaction mixture was poured into saturated aqueous sodium hydrogen carbonate solution and extracted with ethyl acetate. The organic layer was washed with water and saturated aqueous sodium chloride. After drying over anhydrous sodium sulfate, the solvent was evaporated under reduced pressure to give 685 mg of {4-[(E)-2-(2,6-dimethylphenyl)vinyl]-2-oxopiperidin-1-yl}acetaldehyde.

In addition to the compounds described in Examples, the compounds given in Tables 28 to 30 can be obtained by the processes described above, the processes described in Reference Examples and Examples, processes known to ordinary skill in the art and their modifications, without requiring any special experiments. Tables 28 to 30 are placed at the end of the specification, following Tables 1 to 27.

INDUSTRIAL APPLICABILITY

The compounds of the present invention have the sodium channel inhibitory action and are useful as pharmaceuticals, especially therapeutics for diseases associated with sodium channel and symptoms accompanied by these diseases, preferably as analgesics for neuropathic pain.

For example, neuropathic pain means a pain caused by dysfunction of the central or peripheral nervous system and includes diabetic neuropathic pain, etc.

[Pharmacological Tests]

Hereinafter, experiments on the sodium channel inhibitory action using representative compounds of the present invention and animal tests using mice and rats are described in detail.

(Experiment on Sodium Channel Inhibitory Action)

The sodium channel inhibitory action of representative compounds in Compound (I) of the present invention was confirmed by experiment of [$^{14}$C] guanidine uptake using rat brain tissues. The [$^{14}$C] guanidine uptake experiment was performed by the method of Bonisch et al. (British Journal of Pharmacology 108, 436-442, 1993) with some modifications. The [$^{14}$C] guanidine was used as a sodium tracer, and the inhibitory activity on uptake of [$^{14}$C] guanidine induced by veratridine as a sodium channel activator into rat cerebral cortex primary neurons was measured.

a. Preparation of Rat Cerebral Cortex Primary Neuron Culture System

Pregnant rats (Wistar, female, 19 days of gestation) were anesthetized with ether. The animals were bled to death by giving incision through the carotid artery. The fetuses were taken out of the pregnant rats and after ethanol sterilization, the cerebral cortex was removed from the fetuses. The cerebral cortex was digested with papain and dispersed in culture medium, followed by plating on a poly-L-lysine-coated 96-well white plate at a density of $2.5 \times 10^5$ cells/well. Incubation was performed in a $CO_2$ incubator (37° C., 5% $CO_2$) for 2 days.

b. Assessment of Test Compounds

After each well was washed once with an assay buffer (135 mM choline Cl, 5 mM KCl, 1 mM $MgSO_4$, 5.5 mM glucose, 1 mg/mL BSA, 10 mM Hepes-Tris, pH 7.4), a fresh assay buffer was added to the well, followed by incubation at 25° C. for 10 minutes. Then, a reaction solution (a test compound, [$^{14}$C] guanidine and 100 µM, veratridine) was replaced for the buffer, followed by incubation at 25° C. for 15 minutes. The reaction was terminated by washing 3 times with a cold wash buffer (135 mM NaCl, 5 mM KCl, 1 mM $MgSO_4$, 10 mM Hepes-Tris, pH 7.4). To each well, 17 µl of 0.1N NaOH was added. After agitation, 100 µl of scintillator was added to the well and further agitation was continued. The radioactivity was quantified by a liquid scintillation counter. In each experiment, the sodium channel-specific uptake of the whole uptake was designated as portion that was inhibited by 1 mM mexiletine. The action of the test compound on sodium channel is expressed as 50% inhibition concentration ($IC_{50}$) based on the specific uptake.

As shown in Table 31, the compounds of the present invention exhibited excellent inhibitory action.

TABLE 31

| Ex. | Na Channel Inhibition $IC_{50}$ (µM) |
|---|---|
| 24 | 10 |
| 25-2 | 29 |
| 37 | 10 |
| 38 | 6.0 |
| 39 | 16 |
| 40 | 8.4 |
| 51 | 15 |
| 53 | 19 |
| 54 | 19 |
| 56 | 6.7 |
| 62 | 9.2 |
| 63 | 10 |
| 65 | 11 |
| 68 | 8.7 |
| 71 | 7.7 |
| 73 | 1.9 |
| 74 | 7.2 |
| 75 | 3.5 |
| 98 | 12 |
| 103 | 5.0 |

TABLE 31-continued

| Ex. | Na Channel Inhibition IC$_{50}$ (μM) |
|---|---|
| 122 | 9.4 |
| 129 | 4.2 |
| 130 | 3.4 |
| 145 | 6.0 |
| 153 | 2.4 |
| 165 | 2.3 |
| 176 | 2.5 |
| 185 | 6.7 |
| 192 | 1.1 |
| 198 | 8.5 |
| 211 | 3.0 |
| 213 | 3.7 |
| Mexiletine | 70 |

(Analgesic Action on Animal with Streptozotocin-induced Diabetic Neuropathy)

Representative compounds of Compound (I) of the present invention were assessed for the analgesic action in mice with streptozotocin (STZ)-induced diabetic neuropathy to confirm the effect on neuropathic pain. The assessment was performed by the method of Kamei et al. (Pharmacology Biochemistry & Behavior 39, 541-544, 1991) with some modifications.

Male ICR mice of 4 weeks old were intraperitoneally injected with 200 mg/kg weight of STZ to prepare mice with diabetic neuropathic pain. The analgesic action was assessed by the tail pinch test. Specifically, the analgesic action was detected as prolongation in withdrawal latency (in seconds), i.e., the time until the animal showed head-turning response after the tail was pinched with forceps. On Day 14 following the STZ injection, a pretest was carried out to determine the response latency before the administration of a test compound. Only the animals showing not longer than 3 seconds of the response latency in the pretest were used for the test compound assessment on the following day (Day 15 after STZ injection).

In the test compound assessment, the response latency after the administration of a test compound was measured. The test compound was orally administered at a dose of 30 mg/kg, 45 minutes prior to the response latency measurement The analgesic action of a test compound is expressed as prolongation of latency (in seconds) calculated by the formula: (response latency after administration of a test compound)−(response latency before administration of a test compound).

As shown in Table 32, the representative compounds of the present invention displayed the prolongation of latency (in seconds) of about 1 to 5 seconds. Separately, a test was conducted in a similar fashion, using a solvent (10% w/w DMSO/water) in place of the compound of the present invention. The results indicate that the prolongation of latency (in seconds) was 0.69±0.38 second (mean±standard error).

Generally in this analgesic test, the prolongation of at least about 1 second is considered to be effective and when the prolongation is longer than 1.5 second, the activity is rated as excellent; when the prolongation exceeds about 2 seconds, the analgesic action is rated as extremely excellent. Accordingly, the compounds tested in Examples have more excellent activities as compared to those of Comparative Examples 1 and 2. Mexiletine showed the prolongation of about 3 seconds.

TABLE 32

| Ex. | Anti-STZ-induced pain after oral administration: Latency prolongation (in seconds) |
|---|---|
| 24 | 2.6 |
| 37 | 1.9 |
| 38 | 3.1 |
| 39 | 2.9 |
| 49 | 2.2 |
| 53 | 4.2 |
| 62 | 2.3 |
| 63 | 3.3 |
| 65 | 2.3 |
| 71 | 2.3 |
| 74 | 1.8 |
| 87 | 1.6 |
| 99 | 1.7 |
| 101 | 2.0 |
| 102 | 2.1 |
| 105 | 1.8 |
| 108 | 1.8 |
| 110 | 2.1 |
| 114 | 2.4 |
| 125 | 1.6 |
| 126 | 1.5 |
| 134 | 1.7 |
| 135 | 2.4 |
| 150 | 1.7 |
| 170 | 1.7 |
| 179 | 1.8 |
| 180 | 2.3 |
| 189 | 2.4 |
| 203 | 1.7 |
| 204 | 2.4 |
| 205 | 1.6 |
| 209 | 2.0 |
| 210 | 1.5 |
| Comp. Ex. 1 | 0.80 |
| Comp. Ex. 2 | −0.04 |

Comparative Example 1

Compound described in Example 308 (Patent Literature 1: EPC 1254904)

Comparative Example 2

Compound described in Example 334 (Patent Literature 1: EPC 1254904)

(Anti-allodynia Effect in Rats with L5/L6 Spinal Nerve Ligation)

One of the major symptoms in neuropathic pain is a markedly lowered threshold of response to tactile stimulation (allodynia). The anti-allodynia effect of the representative compounds in the compounds of the present invention was confirmed by assessing the analgesic action in L5/L6 spinal nerve ligation rats. The the assessment was performed by the method of Kim and Chung (Pain 50, 355-363, 1992) with some modifications.

Under pentobarbital anesthesia, male SD rats of 5 or 6 weeks old were given surgery to ligate both the left L5 and L6 lumbar nerves tightly with silk threads. For the assessment of analgesic action, the von Frey hair test was adopted. That is, the animal's hindpaw was picked with hair and the lowest strength of hair for limb withdrawal response was designated as a response threshold (log gram) to mechanical stimulation. Since it was confirmed in prior test that the response threshold of the animal's hindpaw ipsilateral to the side of ligation was markedly low during days 7 to 14 after the surgery (in the state of allodynia), the anti-allodynia effect of a test compound was assessed on any day between days 7 and 14 from the surgery. On the day before the assessment of a test compound, the response threshold before administration of a test compound was measured. The animals were divided into 4 to 5 groups so that differences in the mean values of response thresholds before administration among the groups and variation within groups become small. In the assessment of a test compound, the response threshold after administration of the test compound was measured. The test compound was orally given 30 minutes before measurement of the response threshold. The anti-allodynia action potency of a test compound is expressed as $ED_{50}$. In the calculation of the $ED_{50}$, the thresholds of ipsilateral and contralateral paws in the solvent group were designated as 0% and 100%, respectively.

Compounds having excellent $ED_{50}$ values were found in the compounds of the present invention, whereas mexiletine showed $ED_{50}$ value of about 70 mg/kg.

It was confirmed by the test described above that the representative compounds in the compounds of the present invention show the sodium channel inhibitory action. It was also confirmed that these compounds with oral administration exhibited the analgesic action, that was more excellent than that of heretofore known compounds, in the disease animal models, i.e., mice with diabetic neuropathy and L5/L6 spinal nerve ligation rats. Based on the foregoing results, it was confirmed that some compounds of Compound (I) of the present invention showed sodium channel inhibitory action that was more excellent than that of mexiletine. It was also confirmed that some compounds of Compound (I) of the present invention with oral administration showed analgesic action that was equal or superior to that of mexiletine in the animal disease model, i.e., mice with diabetic neuropathy.

Based on the evidence mentioned above, it was confirmed that the compounds of the present invention are excellent sodium channel inhibitors and are useful for relief of pain, especially neuropathic pain such as pain accompanied by diabetic neuropathy, etc.

TABLE 1

| Ex. | R¹ | R³ | R⁴ | Ex. | R¹ | R³ | R⁴ | Ex. | R¹ | R³ | R⁴ |
|---|---|---|---|---|---|---|---|---|---|---|---|
| 1 | H | Me | Cl | 7 | H | MeO | MeO | 12 | Me | Me | Me |
| 2-2 | H | Me | Me | 8 | H | MeO | Cl | 13 | Me₂N | Me | Me |
| 4 | H | Et | Et | 9 | H | F | F | 14 | PhO | Me | Me |
| 5 | H | Me | MeO | 10 | H | F | Cl | 15-2 | Br | Me | Me |
| 6 | H | Me | F | 11 | H | Cl | Cl | 16 | Ph | Me | Me |

TABLE 2

| Ex. | Structure | Salt |
|---|---|---|
| 2-1 | | — |
| 3 | 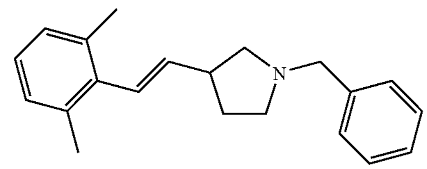 | — |
| 15-1 | 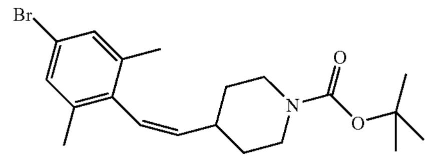 | — |
| 17 | 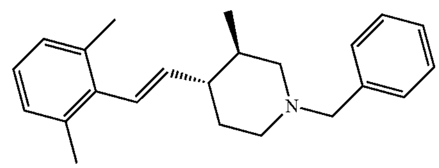 | (CO₂H)₂ |
| 18 | 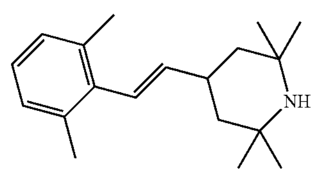 | (CO₂H)₂ |
| 19 | 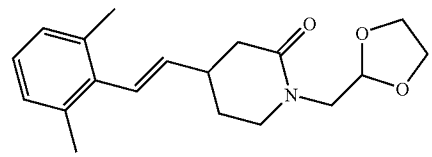 | — |
| 20 | 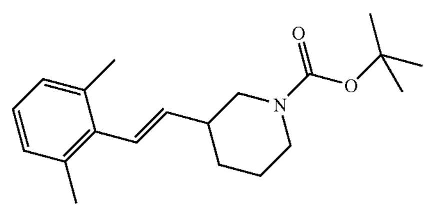 | — |
| 21 | 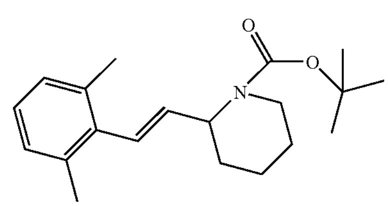 | — |
| 22 | 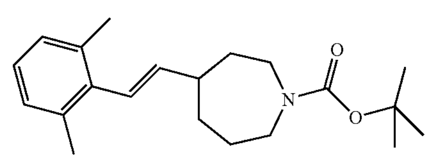 | — |
| 23 | 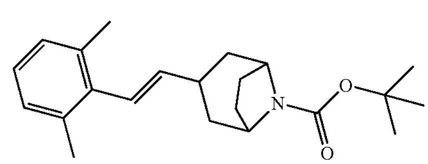 | — |

TABLE 2-continued

| Ex. | Structure | Salt |
|---|---|---|
| 24 | 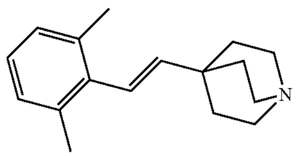 | (CO$_2$H)$_2$ |
| 25-1 | 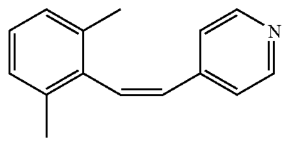 | HCl |
| 25-2 | 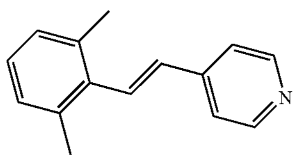 | HCl |
| 26-1 | 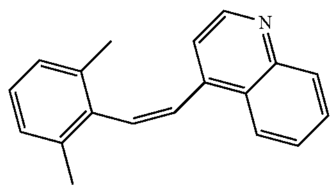 | HCl |

TABLE 3

| Ex. | Structure | Salt |
|---|---|---|
| 26-2 | 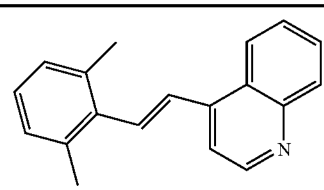 | HCl |
| 27 | 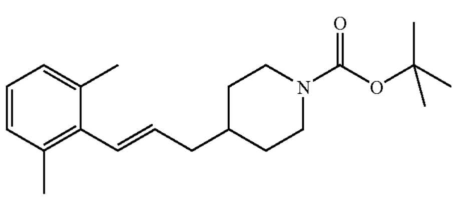 | — |
| 28 | 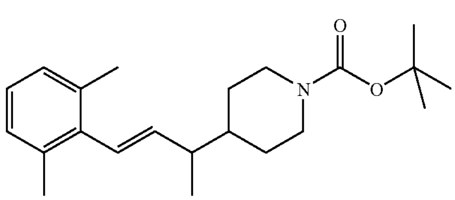 | — |
| 29 | 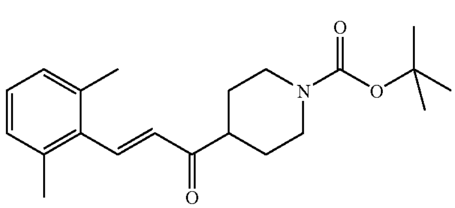 | — |

TABLE 3-continued

| Ex. | Structure | Salt |
|---|---|---|
| 30 | 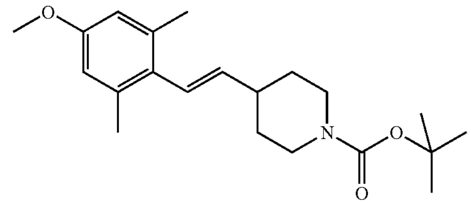 | — |
| 31 | 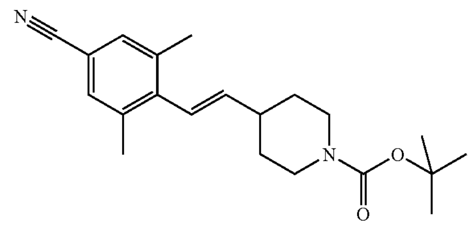 | — |
| 32-1 | 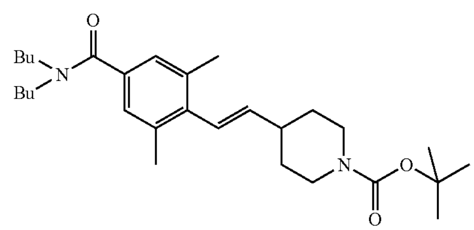 | — |
| 32-2 | 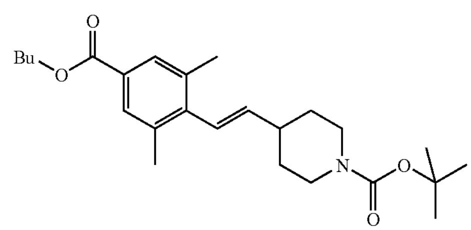 | — |
| 33 | 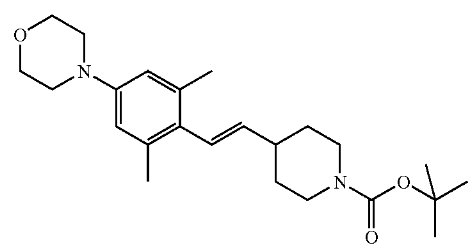 | — |
| 34 | 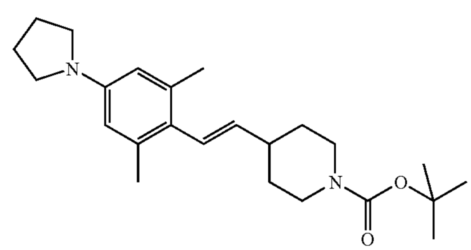 | — |

TABLE 4
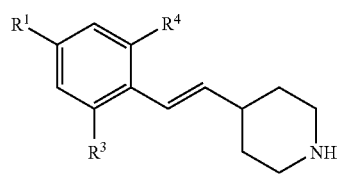
| Ex. | R¹ | R³ | R⁴ | Salt |
|---|---|---|---|---|
| 39 | H | Me | Me | HCl |
| 40 | H | Et | Et | HCl |
| 41 | H | Me | MeO | HCl |
| 42 | H | Me | F | HCl |
| 43 | H | MeO | MeO | (CO₂H)₂ |
| 44 | H | MeO | Cl | HCl |
| 45 | H | F | F | HCl |
| 46 | H | F | Cl | HCl |
| 47 | H | Cl | Cl | HCl |
| 48 | Me | Me | Me | HCl |
| 49 | NC— | Me | Me | HCl |
| 50 | H₂NCO | Me | Me | HCl |
| 51 | Bu₂NCO | Me | Me | HCl |
| 52 | HOOC | Me | Me | HCl |
| 53 | Me₂N | Me | Me | 2HCl |
| 54 | MeO | Me | Me | HCl |
| 55 | PhO | Me | Me | HCl |

TABLE 5-continued

| Ex. | Structure | Salt |
|---|---|---|
| 65 | (2,6-dimethylphenyl)-CH=CH-CH2-piperidin-4-yl (NH) | HCl |
| 66 | (2,6-dimethylphenyl)-CH=CH-CH(Me)-piperidin-4-yl (NH) | 1/2 (CO2H)2 |
| 67 | (2,6-dimethylphenyl)-CH=CH-C(O)-piperidin-4-yl (NH) | HCl |
| 68 | (2,6-dimethylphenyl)-CH=CH-(3-methylpiperidin-4-yl) (NH) | HCl |
| 69 | (2,6-dimethylphenyl)-CH=CH-pyrrolidin-3-yl (NH) | (CO2H)2 |
| 70 | (2,6-dimethylphenyl)-CH=CH-(1-methylpiperidin-2-yl) | HCl |
| 71 | (2,6-dimethylphenyl)-CH=CH-(1-methylpiperidin-3-yl) | (CO2H)2 |

TABLE 6

[Structure: R1, R3, R4 substituted phenyl-CH=CH-CH2-piperidin-4-yl-N-R9]

| Ex. | R1 | R3 | R4 | R9 | Salt |
|---|---|---|---|---|---|
| 72 | H | Me | Me | Me | (CO2H)2 |
| 73 | H | Me | Me | Bn | HCl |
| 74 | H | Me | Me | Me2N(CH2)2 | 2HCl |
| 75 | H | Me | Me | MeO(CH2)2 | (CO2H)2 |
| 76 | H | Me | Me | cPen | HCl |
| 77 | H | Me | Me | Me2(Mo-4-yl)CCO | (CO2H)2 |

TABLE 6-continued

| Ex. | R1 | R3 | R4 | R9 | Salt |
|---|---|---|---|---|---|
| 78 | H | Me | Me | ClCH2CO | — |
| 79 | H | Me | Me | BrCH2CO | — |
| 80 | H | Me | Me | H2C=CHCO | — |
| 81 | H | Me | Me | Cl(CH2)3CO | — |
| 82 | H | Me | Me | [N-ethylcarbonyl-piperazin-N'-yl-CH2-C(O)-] | HCl |
| 83 | H | Me | Me | [N-methylsulfonyl-piperazin-N'-yl-CH2-C(O)-] | HCl |
| 84 | H | Me | Me | [N-acetyl-diazabicyclic-N'-yl-CH2-C(O)-] | (CO2H)2 |
| 85 | H | Me | Me | IM-4-ylCO | HCl |
| 86 | H | Me | Me | 3-Me2NPhCO | HCl |

TABLE 7

[Structure: R1, R3, R4 substituted phenyl-CH=CH-CH2-piperidin-4-yl-N-R9]

| Ex. | R1 | R3 | R4 | R9 | Salt |
|---|---|---|---|---|---|
| 87 | H | Me | Me | [3-amino-1H-1,2,4-triazol-5-yl-C(O)-] | — |
| 88 | H | Me | Me | Py-2-ylCO | HCl |
| 89 | H | Me | Me | Py-3-ylCO | (CO2H)2 |
| 90 | H | Me | Me | 2-NH2Py-3-ylCO | (CO2H)2 |
| 91 | H | Me | Me | 4-H2NPy-3-ylCO | 1/2(CO2H)2 |
| 92 | H | Me | Me | Py-4-ylCO | HCl |
| 93 | H | Me | Me | 3-MeOPy-4-ylCO | (CO2H)2 |
| 94 | H | Me | Me | [1H-benzimidazol-5-yl-C(O)-] | 1/2(CO2H)2 |
| 95 | H | Me | Me | Py-2-ylCH2CO | HCl |

TABLE 7-continued
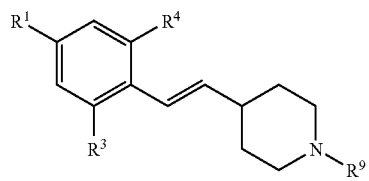
| Ex. | R¹ | R³ | R⁴ | R⁹ | Salt |
|---|---|---|---|---|---|
| 96 | H | MeO | Me | Mo-4-ylCH₂CO | (CO₂H)₂ |
| 97 | H | F | F | Mo-4-ylCH₂CO | (CO₂H)₂ |
| 98 | H | Cl | Cl | Mo-4-ylCH₂CO | (CO₂H)₂ |
TABLE 7-continued
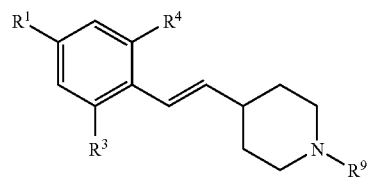
| Ex. | R¹ | R³ | R⁴ | R⁹ | Salt |
|---|---|---|---|---|---|
| 99 | PhO | Me | Me | Mo-4-ylCH₂CO | (CO₂H)₂ |
| 100 | Ph | Me | Me | Mo-4-ylCH₂CO | (CO₂H)₂ |
TABLE 8
| Ex. | Structure | Salt |
|---|---|---|
| 101 | 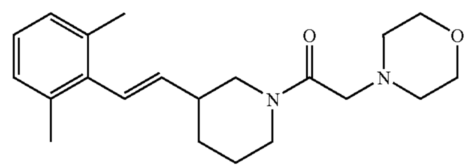 | (CO₂H)₂ |
| 102 | 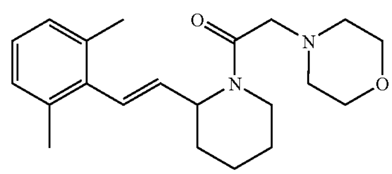 | (CO₂H)₂ |
| 103 | 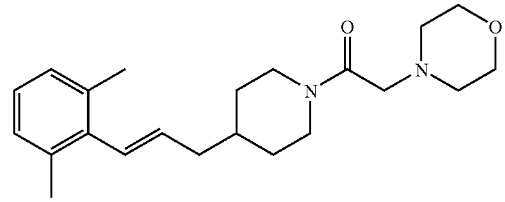 | (CO₂H)₂ |
| 104 | 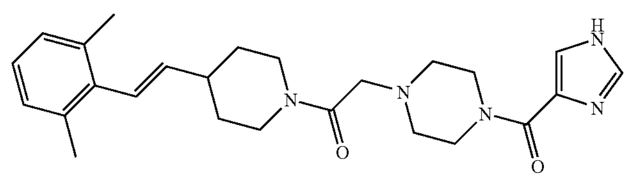 | 2HCl |
| 105 | 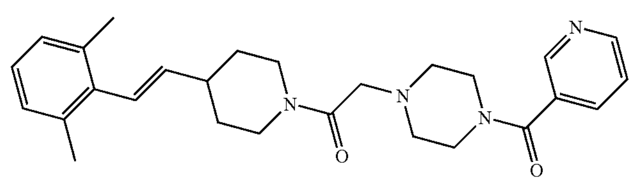 | (CO₂H)₂ |
| 106 | 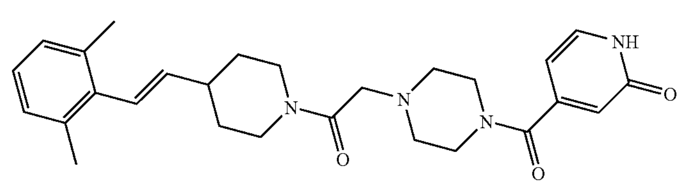 | 2HCl |

TABLE 8-continued

| Ex. | Structure | Salt |
|---|---|---|
| 107 | 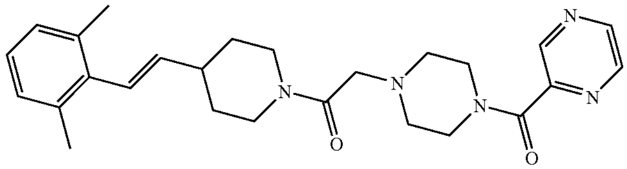 | HCl |
| 108 | 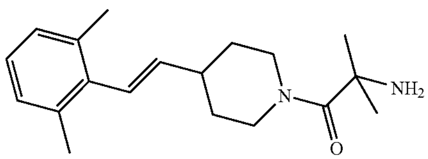 | HCl |
| 109 | 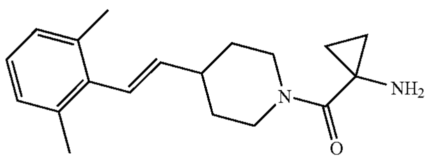 | HCl |
| 110 | 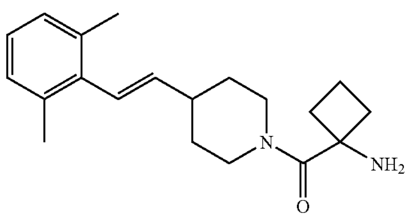 | HCl |
| 111 | 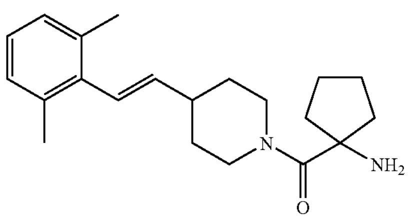 | HCl |
| 112 | 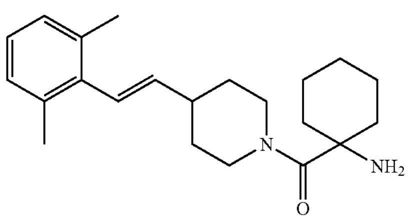 | (CO₂H)₂ |
| 113 | 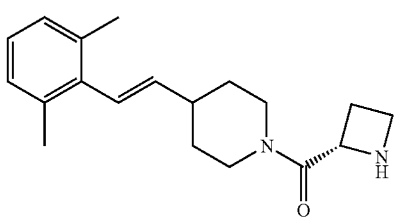 | HCl |
| 114 | 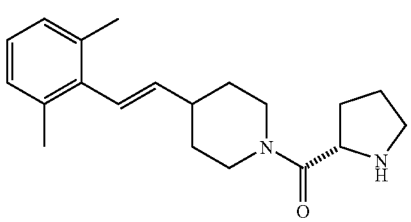 | HCl |

TABLE 8-continued

| Ex. | Structure | Salt |
|---|---|---|
| 115 | 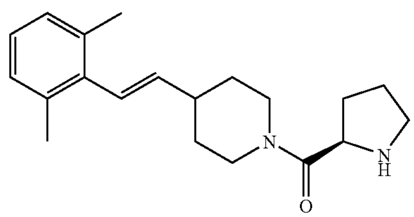 | HCl |
| 116 | 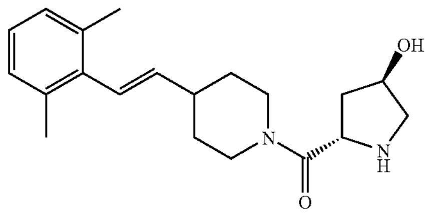 | HCl |
| 117 | 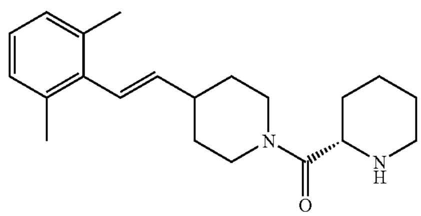 | HCl |
| 118 | 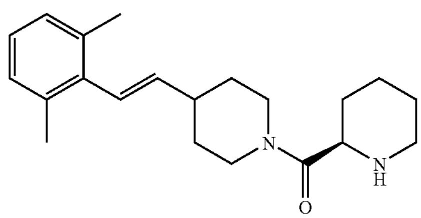 | HCl |
| 119 | 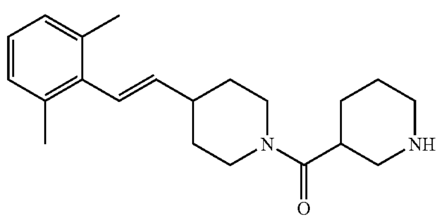 | HCl |

TABLE 9

| Ex. | $R^9$ | Salt |
|---|---|---|
| 120 | Piperi-4-ylCO | HCl |
| 121 | Mo-2-ylCO | HCl |
| 122 | Mo-3-ylCO | HCl |
| 123 | Me(HN=)C | HCl |
| 124 | H$_2$N(HN=)C | HCl |
| 125 | IM-1-ylCH$_2$CO | HCl |
| 126 | | (CO$_2$H)$_2$ |

TABLE 9-continued

Structure: 2,6-dimethylphenyl-CH=CH-piperidine-N-R⁹

| Ex. | R⁹ | Salt |
|---|---|---|
| 127 | (3-tetrahydrofuranyl)NHCH₂CO | HCl |
| 128 | (3-tetrahydrofuranyl)NHCH₂CO (enantiomer) | HCl |
| 129 | (4-tetrahydropyranyl)NHCH₂CO | HCl |
| 130 | (tetrahydrofuran-2-yl)CH₂NHCH₂CO | (CO₂H)₂ |
| 131 | (1-hydroxycyclohexyl)CH₂NHCH₂CO | HCl |
| 132 | (pyridin-4-yl)CH₂NHCH₂CO | 2HCl |
| 133 | H₂NCO-CH(Me)-NHCH₂CO | HCl |
| 134 | AcNH(CH₂)₂NHCH₂CO | HCl |
| 135 | HO(CH₂)₂NHCH₂CO | HCl |
| 136 | MeO(CH₂)₂NHCH₂CO | HCl |
| 137 | Mo-4-yl(CH₂)₂NHCH₂CO | 2HCl |
| 138 | HO(CH₂)₃NHCH₂CO | HCl |
| 139 | 4-ClPh(Me)NCH₂CO | HBr |
| 140 | (1,3-dioxolan-2-yl)CH₂N(Me)CH₂CO | HCl |
| 141 | Et₂NCH₂CO | HBr |
| 142 | Et[MeO(CH₂)₂]NCH₂CO | (CO₂H)₂ |
| 143 | [HO(CH₂)₂]₂NCH₂CO | HCl |
| 144 | Pyrrolid-1-ylCH₂CO | HCl |
| 145 | (2,5-dihydro-1H-pyrrol-1-yl)CH₂CO | HCl |
| 146 | 3-Me₂NPyrrolid-1-ylCH₂CO | 2HCl |
| 147 | 3-HOPyrrolid-1-ylCH₂CO | (CO₂H)₂ |

TABLE 10

Structure: 2,6-dimethylphenyl-CH=CH-piperidine-N-R⁹

| Ex. | R⁹ | Salt |
|---|---|---|
| 148 | 3-EtOPyrrolid-1-ylCH₂CO | (CO₂H)₂ |
| 149 | Piperi-1-ylCH₂CO | HCl |
| 150 | (2-carbamoylpiperidin-1-yl)CH₂CO | HCl |
| 151 | (2-carbamoylpiperidin-1-yl)CH₂CO (S) | HCl |
| 152 | (2-carbamoylpiperidin-1-yl)CH₂CO (R) | HCl |
| 153 | (3,5-dimethylpiperidin-1-yl)CH₂CO | HCl |
| 154 | (3-hydroxymethylpiperidin-1-yl)CH₂CO | (CO₂H)₂ |
| 155 | (3-hydroxymethylpiperidin-1-yl)CH₂CO | (CO₂H)₂ |
| 156 | (3-carbamoylpiperidin-1-yl)CH₂CO | HCl |

TABLE 10-continued

Structure: 2,6-dimethylphenyl-CH=CH-piperidine-N-R⁹

| Ex. | R⁹ | Salt |
|---|---|---|
| 157 | (3R)-3-carbamoylpiperidin-1-ylCH₂CO (H₂N-C(=O)- on piperidine) | HCl |
| 158 | 3-HOPiperi-1-ylCH₂CO | HCl |
| 159 | (3S)-3-hydroxypiperidin-1-ylCH₂CO | HCl |
| 160 | (3R)-3-hydroxypiperidin-1-ylCH₂CO | HCl |
| 161 | 3-MeOPiperi-1-ylCH₂CO | HCl |
| 162 | 3-FPiperi-1-ylCH₂CO | HCl |
| 163 | 3,3-diFPiperi-1-ylCH₂CO | HCl |
| 164 | 4-MePiperi-1-ylCH₂CO | HCl |
| 165 | 4-BnPiperi-1-ylCH₂CO | HCl |
| 166 | 4-H₂NCOPiperi-1-ylCH₂CO | (CO₂H)₂ |
| 167 | 4-HOPiperi-1-ylCH₂CO | (CO₂H)₂ |
| 168 | 4-MeOPiperi-1-ylCH₂CO | HCl |
| 169 | 4-FPiperi-1-ylCH₂CO | HCl |
| 170 | 4-(pyrrolidin-1-yl)piperidin-1-ylCH₂CO | 2HCl |
| 171 | 4-methylpiperazin-1-ylCH₂CO | 2HCl |
| 172 | 4-acetylpiperazin-1-ylCH₂CO | HCl |
| 173 | 4-(2-methoxyethyl)piperazin-1-ylCH₂CO | 2HCl |
| 174 | 4-(2-morpholinoethyl)piperazin-1-ylCH₂CO | 3HCl |
| 175 | 4-(2-morpholino-2-oxoethyl)piperazin-1-ylCH₂CO | 2HCl |

TABLE 11

Structure: 2,6-dimethylphenyl-CH=CH-piperidine-N-R⁹

| Ex. | R⁹ | Salt |
|---|---|---|
| 176 | 4-cyclohexylpiperazin-1-ylCH₂CO | 2HCl |
| 177 | 4-phenylpiperazin-1-ylCH₂CO | HCl |
| 178 | 3-oxopiperazin-1-ylCH₂CO | HCl |
| 179 | Mo-4-ylCH₂CO | HCl |
| 180 | 2-(hydroxymethyl)morpholin-4-ylCH₂CO | HCl |
| 181 | (2S)-2-(hydroxymethyl)morpholin-4-ylCH₂CO | (CO₂H)₂ |
| 182 | (2R)-2-(hydroxymethyl)morpholin-4-ylCH₂CO | (CO₂H)₂ |
| 183 | 2,6-dimethylmorpholin-4-ylCH₂CO | HCl |
| 184 | (2R,6S)-2,6-dimethylmorpholin-4-ylCH₂CO | HCl |
| 185 | ThioMo-4-ylCH₂CO | HCl |
| 186 | 1,1-dioxothiomorpholin-4-ylCH₂CO | HCl |
| 187 | azepan-1-ylCH₂CO | HCl |

TABLE 11-continued

[Structure: 2,6-dimethylphenyl-CH=CH-piperidine-N-R⁹]

| Ex. | R⁹ | Salt |
|---|---|---|
| 188 | Ac-N(homopiperazine)CH₂C(O)CH₃ | HCl |
| 189 | (1,4-oxazepan-4-yl)CH₂C(O)CH₃ | HCl |
| 190 | (isoindolin-2-yl)CH₂C(O)CH₃ | (CO₂H)₂ |
| 191 | (1,4-dioxa-8-azaspiro[4.5]dec-8-yl)CH₂C(O)CH₃ | HCl |
| 192 | (octahydroquinolin-1-yl)CH₂C(O)CH₃ | HCl |
| 193 | (decahydroisoquinolin-2-yl)CH₂C(O)CH₃ | HCl |
| 194 | (1,2,3,4-tetrahydroisoquinolin-2-yl)CH₂C(O)CH₃ | (CO₂H)₂ |
| 195 | (6,7-dimethoxy-1,2,3,4-tetrahydroisoquinolin-2-yl)CH₂C(O)CH₃ | HCl |
| 196 | Mo-4-yl(CH₂)₃CO | HCl |
| 197 | (3-aminopiperidin-1-yl)CH₂C(O)CH₃ | 2HCl |
| 198 | H₂N(CH₂)₂NHCH₂CO | 2HCl |
| 199 | (piperidin-4-ylamino)CH₂C(O)CH₃ | 2HCl |

TABLE 11-continued

[Structure: 2,6-dimethylphenyl-CH=CH-piperidine-N-R⁹]

| Ex. | R⁹ | Salt |
|---|---|---|
| 200 | (3-aminopyrrolidin-1-yl)CH₂C(O)CH₃ | (CO₂H)₂ |
| 201 | (3-aminopyrrolidin-1-yl)CH₂C(O)CH₃ | (CO₂H)₂ |
| 202 | (3-aminopiperidin-1-yl)CH₂C(O)CH₃ | 2HCl |
| 203 | (4-aminopiperidin-1-yl)CH₂C(O)CH₃ | 2HCl |

TABLE 12

[Structure: 2,6-dimethylphenyl-CH=CH-piperidine-N-R⁹]

| Ex. | R⁹ | Salt |
|---|---|---|
| 204 | Pipera-1-ylCH₂CO | 2HCl |
| 205 | (2,5-diazabicyclo[2.2.1]hept-2-yl)CH₂C(O)CH₃ | 2HCl |
| 206 | (homopiperazin-1-yl)CH₂C(O)CH₃ | 2(CO₂H)₂ |
| 207 | N-methyl-N-(tetrahydropyran-4-yl)aminoCH₂C(O)CH₃ | HCl |
| 208 | N-methyl-N-(oxetan-3-yl)aminoCH₂C(O)CH₃ | (CO₂H)₂ |

TABLE 12-continued

[Structure: 2,6-dimethylphenyl-CH=CH-piperidine-N-R⁹]

| Ex. | R⁹ | Salt |
|---|---|---|
| 209 | (3S)-N-Me-N-(tetrahydrofuran-3-yl)-CH₂C(O)Me | HCl |
| 210 | (3R)-N-Me-N-(tetrahydrofuran-3-yl)-CH₂C(O)Me | HCl |
| 211 | N-Me-N-((tetrahydrofuran-2-yl)methyl)-CH₂C(O)Me | (CO₂H)₂ |
| 212 | N-Me-N-((1-hydroxycyclohexyl)methyl)-CH₂C(O)Me | HCl |
| 213 | N-Me-N-(2-morpholinoethyl)-CH₂C(O)Me | 2HCl |
| 214 | (1-Me-pyrrolidin-2-yl)C(O)Me | fum |
| 215 | (2S,4R)-4-hydroxy-1-Me-pyrrolidin-2-yl)C(O)Me | Fum |
| 216 | (1-Me-pyrrolidin-2-yl)C(O)Me | Fum |
| 217 | (1-Me-piperidin-2-yl)C(O)Me | Fum |
| 218 | 1-MePiperi-3-ylCO | HCl |
| 219 | 1-MePiperi-4-ylCO | HCl |
| 220 | 4-MeMo-2-ylCO | HCl |
| 221 | 4-MeMo-3-ylCO | HCl |
| 223 | Mo-4-yl(CH₂)₂ | 2HCl |
| 224 | Et₂N(CH₂)₂ | 2HCl |
| 225 | Mo-4-yl(CH₂)₂CO | HCl |

TABLE 13

| Ex. | STR | Salt |
|---|---|---|
| 222 | [2,6-dimethylstyryl-piperidin-2-one-N-(2-morpholinoethyl)] | (CO₂H)₂ |
| 226 | [2,6-dimethylstyryl-piperidin-2-one-N-CH₂CHO] | — |

TABLE 14

| Ex. | MS | NMR |
|---|---|---|
| 1 | | (CDCl₃): 1.44(11H, m), 1.81(2H, m), 2.32(4H, m), 2.82(2H, m), 4.11(2H, br), 5.80(1H, dd), 6.35(1H, d), 7.02-7.09(2H, m), 7.21(1H, d) |
| 2-1 | | (CDCl₃): 1.24-1.30(2H, m), 1.44-1.61(2H, m), 1.53(9H, s), 1.98(1H, m), 2.21(6H, s), 2.58(2H, m), 3.97(2H, br), 5.55(1H, dd), 6.21(1H, d), 7.03-7.10(3H, m) |
| 2-2 | | (CDCl₃): 1.40-1.47(2H, m), 1.47(9H, s), 1.80(2H, d), 2.27(6H, s), 2.27-2.34(1H, m), 2.82(2H, m), 4.13(2H, br), 5.61(1H, dd), 6.22(1H, d), 7.03-7.07(3H, m) |
| 3 | | (CDCl₃): 1.65-1.73(1H, m), 2.12-2.21(1H, m), 2.26(6H, s), 2.28-2.32(1H, m), 2.51-2.57(1H, m), 2.74-2.80(1H, m), 2.90-3.04(2H, m), 3.61(1H, d), 3.66(1H, d), 5.66(1H, dd), 6.28(1H, d), 7.01(3H, br), 7.22-7.35(5H, m) |
| 4 | | (CDCl₃): 1.14(6H, t), 1.40-1.47(2H, m), 1.47(9H, s), 1.80(2H, m), 2.33(1H, m), 2.62(4H, q), 2.82(2H, m), 4.13(2H, m), 5.57(1H, dd), 6.40(1H, d), 7.04(2H, d), 7.13(1H, m) |
| 5 | | (CDCl₃): 1.40-1.47(2H, m), 1.47(9H, s), 1.80(2H, m), 2.33(4H, br), 2.81(2H, m), 3.80(3H, s), 4.11(2H, m), 6.03(1H, dd), 6.41(1H, d), 6.73(1H, d), 6.80(1H, d), 7.07(1H, t) |

TABLE 14-continued

| Ex. | MS | NMR |
|---|---|---|
| 6 | | (CDCl$_3$): 1.37-1.51(2H, m), 1.47(9H, s), 1.79(2H, m), 2.33(1H, m), 2.33(3H, s), 2.80(2H, m), 4.13(2H, m), 6.14(1H, dd), 6.30(1H, d), 6.86-6.94(2H, m), 7.02-7.07(1H, m) |
| 7 | | (CDCl$_3$): 1.36-1.47(2H, m), 1.46(9H, s), 1.77(2H, m), 2.26(1H, m), 2.79(2H, m), 3.83(6H, s), 4.09(2H, m), 6.53(3H, m), 6.67(1H, d), 7.11(1H, t) |
| 8 | | (CDCl$_3$): 1.37-1.50(2H, m), 1.47(9H, s), 1.79(2H, m), 2.33(1H, m), 2.81(2H, m), 3.83(3H, s), 4.12(2H, m), 6.43(1H, dd), 6.53(1H, d), 6.78(1H, d), 6.99(1H, d), 7.07(1H, t) |
| 9 | | (CDCl$_3$): 1.35-1.47(2H, m), 1.47(9H, s), 1.77(2H, d), 2.29-2.32(1H, m), 2.79(2H, br), 4.14(2H, br), 6.39(1H, d), 6.47(1H, dd), 6.82-6.89(2H, m), 7.07-7.14(1H, m) |
| 10 | | (CDCl$_3$): 1.38-1.47(2H, m), 1.47(9H, s), 1.79(2H, m), 2.33(1H, m), 2.81(2H, m), 4.13(2H, m), 6.37(1H, dd), 6.48(1H, d), 6.97(1H, m), 7.08(1H, m), 7.17(1H, d) |
| 11 | | (CDCl$_3$): 1.20-1.75(2H, m), 1.47(9H, s), 1.82(2H, m), 2.38(1H, m), 2.84(2H, m), 4.12(2H, m), 6.14(1H, dd), 6.34(1H, d), 7.06(1H, t), 7.29(2H, d) |
| 12 | | (CDCl$_3$): 1.38-1.47(2H, m), 1.47(9H, s), 1.78(2H, m), 2.23(9H, s), 2.28(1H, m), 2.81(2H, m), 4.11(2H, m), 5.58(1H, dd), 6.29(1H, d), 6.85(2H, s) |
| 13 | 359 | |
| 14 | 408 | |

TABLE 15

| Ex. | MS | NMR |
|---|---|---|
| 15-1 | 394 | |
| 15-2 | 394 | |
| 16 | 392 | |
| 17 | | 0.91(3H, d), 1.60-1.75(2H, m), 1.77-1.85(1H, m), 1.90-1.97(1H, m), 2.23(6H, s), 2.30-2.45(1H, m), 2.55-2.70(1H, m), 3.13-3.22(2H, m), 4.03(2H, br), 5.47(1H, dd), 6.39(1H, d), 7.01(3H, s), 7.40-7.45(5H, m) |
| 18 | | 1.38(6H, s), 1.44(s), 1.42-1.46(m, total 8H), 1.84(2H, dd), 2.23(6H, s), 2.80-2.90(1H, m), 5.61(1H, dd), 6.43(1H, d), 7.02(3H, s) |
| 19 | (EI) 315 | |
| 20 | | (CDCl$_3$): 1.30-1.65(2H, m), 1.47(9H, s), 1.70-1.80(1H, m), 1.90-2.00(1H, m), 2.29(6H, s), 2.35-2.45(1H, m), 2.55-2.80(2H, m), 3.96(1H, m), 5.55(1H, dd), 6.38(1H, d), 6.95-7.10(3H, m) |
| 21 | | (CDCl$_3$): 1.40-1.80(4H, m), 1.48(9H, s), 1.80-1.90(2H, m), 2.29(6H, s), 2.85-3.00(1H, m), 3.95-4.10(1H, m), 4.98(1H, br), 5.64(1H, dd), 6.34(1H, d), 6.95-7.10(3H, m) |
| 22 | | (300MHz, CDCl$_3$): 1.37-1.43(1H, m), 1.47(9H, s), 1.51-1.71(2H, m), 1.88-2.05(3H, m), 2.26(6H, s), 2.30-2.35(1H, m), 3.19-3.69(4H, m), 5.63(1H, dd), 6.23(1H, d), 7.01(3H, s) |
| 23 | | (300MHz, CDCl$_3$): 1.47(9H, s), 1.60-1.75(6H, m), 1.98-2.01(2H, m), 2.25(6H, s), 2.64-2.78(1H, m), 4.22-4.28(2H, m), 5.49(1H, dd), 6.28(1H, d), 7.01(3H, s) |
| 24 | 242 | 1.88(6H, t), 2.22(6H, s), 3.31(6H, t), 5.66(1H, d), 6.29(1H, d), 7.02(3H, br) |
| 25-1 | | 2.10(6H, s), 6.98(1H, d), 7.10-7.22(3H, m), 7.25(1H, d), 7.42(2H, d), 8.67(2H, d) |
| 25-2 | 210 | 2.37(6H, s), 7.01(1H, d), 7.11-7.20(3H, m), 7.99(1H, d), 8.21-8.25(2H, m), 8.83-8.88(2H, m) |
| 26-1 | | 2.04(6H, s), 7.00-7.20(4H, m), 7.33(1H, d), 7.64(1H, d), 7.89-7.96(1H, m), 8.04-8.11(1H, m), 8.26(1H, d), 8.51(1H, d), 8.83(1H, d) |
| 26-2 | | 2.45(6H, s), 7.14-7.23(3H, m), 7.77(1H, d), 7.89-7.97(1H, m), 8.01(1H, d), 8.10-8.18(1H, m), 8.35-8.46(2H, m), 8.70(1H, d), 9.23(1H, d) |
| 27 | | (CDCl$_3$): 1.18-1.30(2H, m), 1.46(9H, s), 1.70-1.79(2H, m), 2.13-2.28(2H, m), 2.28(6H, s), 2.55-2.75(2H, m), 4.00-4.20(2H, m), 5.63(1H, dt), 6.32(1H, d), 7.03(3H, m) |
| 28 | | (300MHz, CDCl$_3$): 1.04(3H, d), 1.16-1.18(2H, m), 1.38(9H, s), 1.63-1.69(2H, m), 2.10-2.13(2H, m), 2.21(6H, s), 2.89(2H, m), 3.90-4.20(2H, br), 5.44(1H, dd), 6.20(1H, d), 6.95(3H, br) |

TABLE 16

| Ex. | MS | NMR |
|---|---|---|
| 29 | | (CDCl$_3$): 1.47(9H, s), 1.60-1.70(2H, m), 1.86-1.89(2H, m), 2.34(6H, s), 2.71-2.79(1H, m), 2.83-2.88(2H, m), 4.00-4.20(2H, m), 6.45(1H, d), 7.06-7.16(3H, m), 7.79(1H, d) |
| 30 | | (CDCl$_3$): 1.39-1.47(2H, m), 1.49(9H, s), 1.78(2H, m), 2.25(6H, s), 2.32(1H, m), 2.81(2H, m), 3.77(3H, s), 4.12(2H, m), 5.55(1H, dd), 6.26(1H, d), 6.59(2H, s) |
| 31 | 341 | |
| 32-1 | 471 | |
| 32-2 | 416 | |
| 33 | 401 | |
| 34 | 384 | |
| 35 | 359 | |

TABLE 16-continued

| Ex. | MS | NMR |
|---|---|---|
| 36 | 360 | |
| 37 | 236 | 1.57-1.67(2H, m), 1.93(2H, m), 2.31(3H, s), 2.51(1H, m), 2.94(2H, m), 3.28(2H, m), 5.86(1H, dd), 6.37(1H, d), 7.14-7.21(2H, m), 7.29(1H, d) |
| 38 | 216 | 1.48-1.60(4H, m), 1.99-2.07(1H, m), 2.16(6H, s), 2.74(2H, m), 3.15(2H, m), 5.60(1H, dd), 6.28(1H, d), 7.03-7.10(3H, m), 8.79(2H, br) |
| 39 | 216 | 1.57-1.67(2H, m), 1.92(2H, m), 2.23(6H, s), 2.47(1H, m), 2.93(2H, m), 3.27(2H, m), 5.65(1H, dd), 6.40(1H, d), 7.02(3H, s), 8.91(1H, br) |
| 40 | 244 | 1.09(6H, t), 1.56-1.66(2H, m), 1.92(2H, m), 2.50(1H, m), 2.57(4H, q), 2.93(2H, m), 3.28(2H, d), 5.57(1H, dd), 6.45(1H, d), 7.03(2H, d), 7.11(1H, t), 8.87(2H, br) |
| 41 | | 1.54-1.64(2H, m), 1.88(2H, m), 2.27(3H, s), 2.43(1H, m), 2.90(2H, m), 3.25(2H, m), 3.73(3H, s), 5.99(1H, dd), 6.37(1H, d), 6.78(1H, d), 6.82(1H, d), 7.08(1H, t), 8.81(1H, br), 9.06(1H, br) |
| 42 | | 1.58-1.68(2H, m), 1.91(2H, m), 2.32(3H, s), 2.48(1H, m), 2.92(2H, m), 3.27(2H, m), 6.10(1H, dd), 6.35(1H, d), 6.99-7.05(2H, m), 7.13-7.18(2H, m), 9.05(2H, br) |
| 43 | | 1.52(2H, m), 1.84(2H, m), 2.38(1H, m), 2.89(2H, m), 3.27(2H, m), 3.73(6H, s), 6.45(1H, dd), 6.59(1H, d), 6.66(2H, m), 7.16(1H, m) |
| 44 | | 1.54-1.64(2H, m), 1.90(2H, m), 2.47(1H, m), 2.92(2H, m), 3.28(2H, m), 3.82(3H, s), 6.39(1H, dd), 6.47(1H, d), 7.02(1H, d), 7.05(1H, d), 7.22(1H, t), 8.92(2H, br) |
| 45 | | 1.57-1.67(2H, m), 1.90(2H, d), 2.50(1H, m), 2.91(2H, m, dt), 3.28(2H, d), 6.36(1H, d), 6.42(1H, dd), 7.08-7.15(2H, m), 7.29-7.37(1H, m), 9.03(2H, br) |
| 46 | | 1.54-1.64(2H, m), 1.90(2H, m), 2.50(1H, m), 2.92(2H, m), 3.27(2H, m), 6.32(1H, dd), 6.43(1H, d), 7.21-7.35(3H, m), 8.80(2H, br) |

TABLE 17

| Ex. | MS | NMR |
|---|---|---|
| 47 | | 1.58-1.69(2H, m), 1.94(2H, m), 2.54(1H, m), 2.94(2H, dt), 3.28(2H, d), 6.11(1H, dd), 6.36(1H, d), 7.29(1H, t), 7.49(2H, d), 8.92(2H, br) |
| 48 | | 1.57-1.67(2H, m), 1.91(2H, d), 2.19(9H, s), 2.46(1H, m), 2.92(2H, m), 3.26(2H, d), 5.60(1H, dd), 6.33(1H, d), 6.83(2H, s), 8.99(2H, br) |
| 49 | 241 | 1.57-1.68(2H, m), 1.91-1.95(2H, m), 2.27(6H, s), 2.49-2.53(1H, m), 2.89-2.98(2H, m), 3.26-3.29(2H, m), 5.79(1H, dd), 6.38(1H, d), 7.52(2H, s), 8.78-9.07(2H, br) |
| 50 | 259 | |
| 51 | 371 | 0.74-1.66(16H, m), 1.92-1.95(2H, m), 2.25(6H, s), 2.50-2.51(1H, m), 2.93-2.99(2H, m), 3.15(2H, br), 3.28-3.39(4H, m), 5.71(1H, dd), 6.38(1H, d), 6.97(2H, s), 8.50-8.82(2H, br) |
| 52 | 260 | |
| 53 | 259 | 1.55-1.66(2H, m), 1.91-1.93(2H, m), 2.25(6H, s), 2.49-2.54(1H, m), 2.89-3.00(8H, m), 3.26-3.29(2H, m), 5.65(1H, dd), 6.33(1H, d), 7.03(2H, br), 8.69-8.96(2H, br) |
| 54 | 246 | 1.56-1.65(2H, m), 1.91(2H, m), 2.21(6H, s), 2.45(1H, m), 2.93(2H, m), 3.27(2H, m), 3.70(3H, s), 5.58(1H, dd), 6.30(1H, d), 6.61(2H, m), 8.65(1H, br), 8.95(1H, s) |
| 55 | 308 | |
| 56 | 294 | 1.45-1.59(4H, m), 1.97-2.05(1H, m), 2.15(6H, s), 2.74-2.79(2H, m), 3.14-3.17(2H, m), 5.63(1H, d), 6.21(1H, d), 7.28(2H, s), 8.63(1H, br) |
| 57 | 294 | |
| 58 | 292 | |
| 59 | 285 | |
| 60 | 301 | |
| 61 | | 1.35-1.50(1H, m), 1.90-2.00(1H, m), 2.00-2.20(1H, m), 2.24(6H, s), 2.65-3.00(3H, m), 3.45-3.65(2H, m), 5.80(1H, dd), 6.46(1H, d), 7.00-7.10(3H, m), 9.62(1H, br), 9.83(1H, br) |
| 62 | 216 | 1.40-1.55(1H, m), 1.55-1.75(1H, m), 1.80-2.10(4H, m), 2.31(6H, s), 2.20-2.30(1H, m), 3.27(1H, m), 3.65-3.75(1H, m), 5.94(1H, dd), 6.79(1H, d), 6.90-7.15(3H, m), 9.60(1H, br), 9.86(1H, br) |
| 63 | 230 | 1.50-1.60(1H, m), 1.74-2.07(5H, m), 2.23(6H, s), 2.46-2.52(1H, m), 3.03-3.26(4H, m), 5.66(1H, dd), 6.32(1H, d), 7.01(3H, s), 8.92(2H, br) |
| 64 | | 1.75-1.81(4H, m), 1.91-2.01(4H, m), 2.22(6H, s), 2.67-2.75(1H, m), 3.98(2H, br), 5.54(1H, dd), 6.38(1H, d), 7.02(3H, s), 8.84(2H, br) |
| 65 | 230 | 1.40(2H, m), 1.69(1H, m), 1.84(2H, m), 2.18(2H, t), 2.24(6H, s), 2.84(2H, m), 3.30(2H, m), 5.65(1H, dd), 6.38(1H, d), 7.04(3H, m), 8.70(1H, br), 8.93(1H, br) |
| 66 | | 1.07(3H, d), 1.15-1.30(2H, m), 1.35-1.45(1H, m), 1.68-1.77(2H, m), 2.15-2.20(1H, m), 2.24(6H, s), 2.51-2.67(2H, m), 3.08-3.15(2H, m), 5.53(1H, dd), 6.30(1H, d), 7.01(3H, br) |

TABLE 18

| Ex. | MS | NMR |
|---|---|---|
| 67 | | 1.65-1.80(2H, m), 1.95-2.05(2H, m), 2.31(6H, s), 2.98-3.01(2H, m), 3.10-3.18(1H, m), 3.24-3.32(2H, m), 6.56(1H, d), 7.08-7.18(3H, m), 7.76(1H, d), 8.88(1H, br), 9.14(1H, br) |

TABLE 18-continued

| Ex. | MS | NMR |
|---|---|---|
| 68 | 230 | 0.95(3H, d), 1.65-1.85(3H, m), 2.04-2.13(1H, m), 2.25(6H, s), 2.57(1H, m), 2.88(1H, m), 3.20-3.30(2H, m), 5.47(1H, dd), 6.40(1H, d), 7.02(3H, s), 9.04(2H, br), 9.23(1H, br) |
| 69 | | 1.70-1.80(1H, m), 2.07-2.18(1H, m), 2.23(6H, s), 2.85-2.90(1H, m), 2.95-3.15(2H, m), 3.19-3.25(1H, m), 3.31-3.36(1H, m), 5.67(1H, dd), 6.46(1H, d), 7.02(3H, br) |
| 70 | | 1.45-1.65(1H, m), 1.80-1.90(1H, m), 1.90-2.10(2H, m), 2.28(6H, s), 2.30-2.50(2H, m), 2.71(1H, br), 2.80(3H, s), 3.25-3.45(1H, m), 3.55-3.65(1H, m), 6.11(1H, dd), 6.71(1H, d), 7.00-7.15(3H, m), 12.55(1H, br) |
| 71 | 230 | 1.30-1.40(1H, m), 1.90-2.00(1H, m), 2.00-2.20(2H, m), 2.25(6H, s), 2.35-2.80(2H, m), 2.84(3H, s), 2.90-3.10(1H, m), 3.60-3.80(2H, m), 5.44(1H, dd), 6.49(1H, d), 6.95-7.10(3H, m) |
| 72 | | 1.85-2.15(4H, m), 2.25(6H, s), 2.30-2.45(1H, m), 2.70-3.10(2H, m), 2.82(3H, s), 3.70-3.80(2H, m), 5.50-5.65(1H, m), 6.40(1H, d), 6.95-7.10(3H.m) |
| 73 | 306 | 1.70-1.85(2H, m), 1.89-2.00(2H, m), 2.19-2.23(6H, m), 2.36-2.47(1H, m), 2.92-3.09(2H, m), 3.20-3.40(2H, m), 4.25-4.38(2H, m), 5.57-5.84(1H, m), 6.33-6.46(1H, m), 7.00-7.03(3H, m), 7.44-7.50(3H, m), 7.58-7.64(2H, m), 10.30-10.70(1H, m) |
| 74 | 287 | 1.70-1.85(2H, m), 1.95-2.10(2H, m), 2.23(6H, s), 2.40-2.50(1H, m), 2.85(6H, s), 2.95-3.75(8H, m), 5.64(1H, dd), 6.39(1H, d), 7.02(3H, s), 10.35-10.75(2H, m) |
| 75 | 274 | 1.60-1.80(2H, m), 1.88-2.00(2H, m), 2.23(6H, s), 2.36-2.48(1H, m), 2.85-3.02(2H, m), 3.14-3.23(2H, m), 3.31(3H, s), 3.35-3.45(2H, m), 3.64(3H, t), 5.65(1H, dd), 6.37(1H, d), 7.02(3H, s) |
| 76 | | 1.48-1.62(2H, m), 1.65-2.12(10H, m), 2.21-2.27(6H, m), 2.40-2.50(1H, m), 2.88-3.17(2H, m), 3.37-3.70(3H, m), 5.59-5.89(1H, m), 6.34-6.48(1H, m), 7.02(3H, s), 10.25-10.65(1H, m) |
| 77 | 371 | |
| 78 | 292 | |
| 79 | 336 | |
| 80 | 270 | |
| 81 | 320 | |
| 82 | 398 | |
| 83 | 420 | |

TABLE 19

| Ex. | MS | NMR |
|---|---|---|
| 84 | 396 | |
| 85 | | 1.30-1.60(2H, m), 1.80-1.95(2H, m), 2.23(6H, s), 2.50-2.58(1H, m), 2.80-3.55(2H, m), 4.10-4.60(2H, m), 5.68(1H, dd), 6.37(1H, d), 7.01(3H, s), 8.09(1H, s), 9.06(1H, s) |
| 86 | 363 | |
| 87 | 326 | 1.27-1.45(2H, m), 1.72-1.90(2H, m), 2.22(6H, s), 2.45-2.55(1H, m), 2.75-2.95(1H, m), 3.05-3.22(1H, m), 4.07-4.28(1H, m), 4.38-4.50(1H, m), 5.65(1H, dd), 6.00-6.20(2H, br), 6.34(1H, d), 7.00(3H, s), 12.23(1H, br) |
| 88 | | 1.36-1.52(2H, m), 1.67-1.78(1H, m), 1.84-1.96(1H,, m), 2.23(6H, s), 2.45-2.55(1H, m), 2.88-3.00(1H, m), 3.08-3.21(1H, m), 3.60-3.72(1H, m), 4.45-4.57(1H, m), 5.67(1H, dd), 6.35(1H, d), 7.01(3H, s), 7.53-7.58(1H, m), 7.63(1H, d), 7.98-8.06(1H, m), 8.64(1H, d) |
| 89 | | 1.36-1.52(2H, m), 1.66-1.96(2H, m), 2.23(6H, s), 2.80-3.80(4H, m), 4.40-4.60(1H, m), 5.67(1H, dd), 6.36(1H, d), 7.01(3H, s), 7.48(1H, dd), 7.81-7.88(1H, m), 8.55-8.70(2H, m) |
| 90 | | 1.32-1.53(2H, m), 1.70-1.87(2H, m), 2.23(6H, s), 2.40-2.55(1H, m), 2.80-3.20(2H, m), 5.65(1H, dd), 6.35(1H, d), 6.60-6.67(1H, m), 7.01(3H, s), 7.42-7.48(1H, m), 7.96-7.84(1H, m) |
| 91 | 336 | |
| 92 | | 1.36-1.55(2H, m), 1.66-1.78(1H, m), 1.85-1.96(1H, m), 2.23(6H, s), 2.45-2.55(1H, m), 2.90-3.03(1H, m), 3.10-3.22(1H, m), 3.37-3.50(1H, m), 4.43-4.53(1H, m), 5.67(1H, dd), 6.36(1H, d), 7.01(3H, s), 7.84(2H, d), 8.89(2H, d) |
| 93 | 351 | |
| 94 | 360 | |
| 95 | 335 | |
| 96 | 359 | |
| 97 | 351 | |
| 98 | 383 | 1.25(1H, m), 1.44(1H, m), 1.82(2H, m), 2.54(1H, m), 2.75(5H, m), 3.12(1H, m), 3.60(1H, m), 3.69(5H, m), 3.89(1H, m), 4.34(1H, m), 6.12(1H, dd), 6.32(1H, d), 7.27(1H, t), 7.48(2H, d) |
| 99 | 435 | |
| 100 | 419 | |
| 101 | 343 | 1.30-1.98(4H, m), 2.20-2.50(7H, m), 2.50-3.10(6H, m), 3.40-4.00(7H, m), 4.24(1H, m), 5.62(1H, dt), 6.42(1H, t), 6.99-7.03(3H, m) |
| 102 | 343 | 1.24-2.00(6H, m), 2.20-2.64(6H, m), 2.60-2.35(1H, m), 2.78(4H, m), 3.15-3.50(1H, m), 3.63-4.36(6H, m), 4.80-5.42(1H, m), 5.63-5.81(1H, m), 6.83(1H, m), 7.03(3H, m) |

TABLE 20

| Ex. | MS | NMR |
|---|---|---|
| 103 | 357 | 1.03(1H, m), 1.19(1H, m), 1.52-1.73(3H, m), 2.10-2.28(2H, m), 2.24(6H, s), 2.61(1H, m), 2.76(4H, m), 3.00(1H, m), 3.58(1H, m), 3.68(4H, m), 3.70(1H, m), 3.86(1H, m), 4.35(1H, m), 5.66(1H, dt), 6.34(1H, d), 7.00(3H, s) |
| 104 | 436 | |
| 105 | 447 | 1.18-1.50(2H, m), 1.74-1.88(2H, m), 2.22(6H, s), 2.40-2.50(1H, m), 2.62-2.82(5H, m), 3.05-3.17(1H, m), 3.30-4.00(7H, m), 4.30-4.40(1H, m), 5.65(1H, dd), 6.34(1H, d), 7.01(3H, s), 7.49(1H, dd), 7.84(1H, dt), 8.62(1H, d), 8.66(1H, dd) |
| 106 | 463 | |
| 107 | 448 | |
| 108 | 301 | 1.23-1.40(2H, m), 1.58(6H, s), 1.80-1.90(2H, m), 2.23(6H, s), 2.45-2.55(1H, m), 2.80-3.20(2H, m), 4.10-4.40(2H, m), 5.65(1H, dd), 6.34(1H, d), 7.01(3H, s), 8.19(2H, br) |
| 109 | 299 | |
| 110 | 313 | 1.40-1.43(2H, m), 1.76-1.85(3H, m), 2.13-2.26(7H, m), 2.30-2.39(2H, m), 2.47-2.51(1H, m), 2.65-2.72(2H, m), 3.01(2H, br), 4.04(2H, br), 5.65(1H, dd), 6.36(1H, d), 7.01(3H, s), 8.89(2H, br) |
| 111 | 327 | |
| 112 | 341 | |
| 113 | 299 | |
| 114 | 313 | 1.25-1.48(2H, m), 1.72-1.97(2H, m), 2.22(6H, s), 2.33-2.43(1H, m), 2.78-2.87(1H, m), 3.12-3.34(3H, m), 3.83-3.92(1H, m), 4.53-4.66(1H, m), 4.31-4.40(1H, m), 5.66(1H, dd), 6.36(1H, d), 7.01(3H, s) |
| 115 | 313 | |
| 116 | 329 | |
| 117 | 327 | |
| 118 | 327 | |
| 119 | 327 | |
| 120 | 327 | |
| 121 | 329 | |
| 122 | 329 | 1.21-1.49(2H, m), 1.79-1.93(2H, m), 2.23(6H, s), 2.49-2.51(1H, m), 2.73-2.90(1H, m), 3.10-3.35(3H, m), 3.43-3.54(3H, m), 3.66-3.75(1H, m), 3.84-3.97(2H, m), 4.04-4.15(1H, m), 4.24-4.44(2H, m), 5.61-5.67(1H, m), 6.33-6.38(1H, m), 7.02(3H, s), 9.35(1H, br) |
| 123 | | 1.40-1.62(2H, m), 1.85-1.96(2H, m), 2.23(6H, s), 2.30(3H, s), 2.50-2.63(1H, m), 3.15-3.35(2H, m), 3.80-4.30(2H, m), 5.65(1H, dd), 6.37(1H, d), 7.02(3H, s), 9.01(2H, br) |

TABLE 21

| Ex. | MS | NMR |
|---|---|---|
| 124 | | 1.34-1.47(2H, m), 1.78-1.89(2H, m), 2.23(6H, s), 2.44-2.50(1H, m), 3.04-3.16(2H, m), 3.85-3.95(2H, m), 5.66(1H, dd), 6.35(1H, d), 7.01(3H, s), 7.50(4H, br) |
| 125 | 324 | 1.25-1.38(1H, m), 1.44-1.56(1H, m), 1.79-1.94(2H, m), 2.24(6H, s), 2.49-2.52(1H, m), 2.76-2.85(1H, m), 3.16-3.26(1H, m), 3.80-3.88(1H, m), 4.28-4.36(1H, m), 5.30-5.43(2H, m), 5.67(1H, dd), 6.36(1H, d), 7.02(3H, s), 7.62-7.66(2H, m), 9.02(1H, m) |
| 126 | 329 | 1.20-1.47(2H, m), 1.78-1.86(2H, m), 2.22(6H, s), 2.44-2.52(1H, m), 2.72-2.82(1H, m), 3.04-3.14(1H, m), 3.67-3.75(1H, m), 3.78-3.92(2H, m), 4.16-4.25(1H, m), 4.32-4.40(1H, m), 4.53-4.59(2H, m), 4.61-4.68(2H, m), 5.65(1H, dd), 6.34(1H, d), 7.01(3H, s) |
| 127 | 343 | |
| 128 | 343 | |
| 129 | 357 | 1.22-1.32(1H, m), 1.36-1.48(1H, m), 1.56-1.68(2H, m), 1.83-1.88(2H, m), 1.95-2.02(2H, m), 2.23(6H, s), 2.49-2.51(1H, m), 2.76-2.86(1H, m), 3.10-3.34(4H, m), 3.73-3.80(1H, m), 3.88-3.94(2H, m), 4.02-4.15(2H, m), 4.34-4.46(1H, m), 5.66(1H, dd), 6.35(1H, d), 7.02(3H, s), 8.90(1H, br) |
| 130 | 357 | 1.20-1.47(2H, m), 1.50-1.60(1H, m), 1.78-1.90(4H, m), 1.95-2.04(1H, m), 2.22(6H, s), 2.46-2.52(1H, m), 2.74-2.92(2H, m), 2.96-3.04(1H, m), 3.04-3.16(1H, m), 3.64-3.74(2H, m), 3.75-3.83(2H, m), 3.94-4.08(2H, m), 4.08-4.18(1H, m), 4.33-4.40(1H, m), 5.66(1H, dd), 6.34(1H, d), 7.01(3H, s) |
| 131 | 385 | |
| 132 | 364 | |
| 133 | 344 | |
| 134 | 358 | 1.20-1.47(2H, m), 1.81-1.89(5H, m), 2.23(6H, s), 2.49-2.52(1H, m), 2.76-2.86(1H, m), 2.95-3.01(2H, m), 3.09-3.18(1H, m), 3.30-3.39(2H, m), 3.65-3.73(1H, m), 4.02-4.16(2H, m), 4.32-4.41(1H, m), 5.65(1H, dd), 6.35(1H, d), 7.01(3H, s), 8.12-8.19(1H, m), 8.81(1H, br) |
| 135 | 317 | 1.24-1.34(1H, m), 1.34-1.48(1H, m), 1.80-1.89(2H, m), 2.23(6H, s), 2.49-2.52(1H, m), 2.77-2.86(1H, m), 2.99-3.03(2H, m), 3.10-3.18(1H, m), 3.65-3.73(3H, m), 4.01-4.14(2H, m), 4.33-4.40(1H, m), 5.16-5.22(1H, m), 5.65(1H, dd), 6.35(1H, d), 7.01(3H, s), 8.75(1H, br) |
| 136 | 331 | |
| 137 | 386 | |
| 138 | 331 | |

TABLE 21-continued

| Ex. | MS | NMR |
|---|---|---|
| 139 | 397 | |
| 140 | 373 | |
| 141 | 329 | |
| 142 | 359 | |

TABLE 22

| Ex. | MS | NMR |
|---|---|---|
| 143 | 361 | |
| 144 | 327 | |
| 145 | 325 | 1.23-1.37(1H, m), 1.38-1.50(1H, m), 1.79-1.88(2H, m), 2.22(6H, s), 2.46-2.52(1H, m), 2.76-2.85(1H, m), 3.28-3.36(4H, m), 3.08-3.18(1H, m) 3.58-3.66(1H, m), 4.33-4.40(1H, m), 4.41-4.55(2H, m), 5.65(1H, dd), 5.91(2H, s), 6.35(1H, d), 7.01(3H, s), 10.57(1H, br) |
| 146 | 370 | |
| 147 | 343 | |
| 148 | 371 | |
| 149 | 341 | |
| 150 | 384 | 1.23-1.52(2H, m), 1.52-1.75(2H, m), 1.75-2.05(3H, m), 2.05-2.20(1H, m), 2.23(6H, s), 2.45-2.53(1H, m), 2.76-2.90(1H, m), 3.08-3.18(2H, m), 3.30-3.35(1H, m), 3.40-3.57(1H, m), 3.65-3.80(1H, m), 3.98-4.42(4H, m), 5.16-5.22(1H, m), 5.65(1H, dd), 6.35(1H, d), 7.01(3H, s), 7.57-7.88(1H, m), 7.00-8.10(1H, m), 9.11-9.47(1H, m) |
| 151 | 384 | |
| 152 | 384 | |
| 153 | 369 | 0.74-0.84(1H, m), 0.88(6H, m), 1.13-1.17(1H, m), 1.22-1.50(2H, m), 1.70-1.90(2H, m), 1.79-1.88(3H, m), 1.94-2.08(1H, m), 2.21(6H, s), 2.49-2.52(1H, m), 2.78-2.86(1H, m), 3.11-3.19(1H, m) 3.31-3.33(3H, m), 3.60-3.69(1H, m), 4.20-4.42(2H, m), 5.65(1H, dd), 6.35(1H, d), 7.01(3H, s), 9.58(1H, br) |
| 154 | 371 | |
| 155 | 371 | |
| 156 | 384 | |
| 157 | 384 | |
| 158 | 357 | |
| 159 | 357 | |
| 160 | 357 | |
| 161 | 371 | |
| 162 | 359 | |
| 163 | 377 | |
| 164 | 355 | |
| 165 | 431 | 1.21-1.35(1H, m), 1.35-1.65(3H, m), 1.65-1.88(2H, m), 1.79-1.88(2H, m), 2.21(6H, s), 2.48-2.55(3H, m), 2.78-3.00(2H, m), 3.15-3.19(1H, m), 3.30-3.38(4H, m), 3.40-3.51(1H, m), 3.58-3.68(1H, m), 4.18-4.40(2H, m), 5.65(1H, dd), 6.35(1H, d), 7.01(3H, s), 7.16-7.23(3H, m), 7.26-7.34(1H, m), 9.36(1H, br) |

TABLE 23

| Ex. | MS | NMR |
|---|---|---|
| 166 | 384 | |
| 167 | 357 | |
| 168 | 371 | |
| 169 | 359 | |
| 170 | 410 | 1.22-1.52(2H, m), 1.81-2.02(6H, m) 2.23(10H, m), 2.47-2.53(1H, m) 2.75-2.87(1H, m), 2.94-3.20(4H, m), 3.26-3.70(7H, m), 4.20-4.46(3H, m), 5.66(1H, dd), 6.36(1H, d), 7.01(3H, s), 9.99(1H, br), 11.66(1H, s) |
| 171 | 356 | |
| 172 | 384 | |
| 173 | 400 | |
| 174 | 455 | |
| 175 | 469 | |
| 176 | 424 | 1.06-1.18(1H, m), 1.18-1.50(6H, m), 1.57-1.67(1H, m), 1.78-1.88(4H, m), 2.08-2.16(2H, m), 2.46-2.52(2H, m), 2.76-2.86(1H, m), 3.09-3.17(1H, s), 3.17-3.76(12H, m), 4.18-4.55(2H, m), 5.65(1H, dd), 6.35(1H, d), 7.01(3H, s) |
| 177 | 418 | |
| 178 | 356 | |
| 179 | 343 | 1.20-1.55(2H, m), 1.78-1.92(2H, m), 2.23(6H, s), 2.45-2.55(1H, m), 2.76-2.88(1H, m), 3.08-3.52(5H, m), 3.60-4.05(5H, m), 4.30-4.50(3H, m), 5.65(1H, dd), 6.35(1H, d), 7.01(3H, s), 10.23(1H, br) |
| 180 | 373 | 1.23-1.52(2H, m), 1.82-1.91(2H, m), 2.23(6H, s), 2.49-2.52(1H, m), 2.78-3.00(2H, m), 3.04-3.22(2H, m), 3.31-3.52(4H, m), 3.59-3.71(1H, m), 3.76-4.04(3H, m), 4.31-4.50(3H, m), 5.02(1H, br), 5.66(1H, dd), 6.36(1H, d), 7.02(3H, s), 10.23(1H, br) |

TABLE 23-continued

| Ex. | MS | NMR |
|---|---|---|
| 181 | 373 | |
| 182 | 373 | |
| 183 | 371 | |
| 184 | 371 | |
| 185 | 359 | 1.25-1.35(1H, m), 1.38-1.51(1H, m), 1.80-1.91(2H, m), 2.23(6H, s), 2.49-2.52(1H, m), 2.77-2.96(3H, m), 3.11-3.35(5H, m), 3.57-3.73(3H, m), 4.28-4.45(3H, m), 5.65(1H, dd), 6.35(1H, d), 7.01(3H, s), 9.83(1H, br) |
| 186 | 391 | |
| 187 | 355 | |
| 188 | 398 | |

TABLE 24

| Ex. | MS | NMR |
|---|---|---|
| 189 | 357 | 1.29-1.50(2H, m), 1.84-1.87(2H, m), 2.07-2.23(8H, m), 2.49-2.50(1H, m), 2.79-2.85(1H, m), 3.11-3.17(1H, m), 3.32-3.47(4H, m), 3.65-3.73(3H, m), 3.86(2H, br), 4.36-4.46(3H, m), 5.65(1H, dd), 6.35(1H, d), 7.01(3H, s), 9.76(1H, br) |
| 190 | 375 | |
| 191 | 399 | |
| 192 | 395 | 0.97-1.10(1H, m), 1.10-1.89(13H, m), 2.08-2.25(7H, m), 2.46-2.52(1H, m), 2.78-3.40(5H, m), 3.46-3.56(1H, m), 3.68-3.80(1H, m), 3.85-3.95(1H, m), 4.06-4.20(1H, m), 4.27-4.50(2H, m), 5.65(1H, dd), 6.36(1H, d), 7.01(3H, s), 9.22(1H, br) |
| 193 | 395 | |
| 194 | 389 | |
| 195 | 449 | |
| 196 | 371 | |
| 197 | 356 | |
| 198 | 316 | 1.20-1.34(1H, m), 1.37-1.49(1H, m), 1.80-1.88(2H, m), 2.23(6H, s), 2.49-2.51(1H, m), 2.77-2.86(1H, m), 3.10-3.25(5H, m), 3.66-3.75(1H, m), 4.09-426(2H, m), 4.31-4.40(1H, m), 5.65(1H, dd), 6.36(1H, d), 7.01(3H, s), 8.36(1H, br) |
| 199 | 356 | |
| 200 | 342 | |
| 201 | 342 | |
| 202 | 356 | |
| 203 | 356 | 1.28-1.30(1H, m), 1.43-1.45(1H, m), 1.83-1.86(2H, m), 2.02-2.23(10H, m), 2.50-2.51(1H, m), 2.79-2.85(1H, m), 3.12-3.75(7H, m), 4.26-4.39(3H, m), 5.65(1H, dd), 6.35(1H, d), 7.02(3H, s), 8.65(3H, br), 9.90(1H, br) |
| 204 | 342 | 1.22-1.37(1H, m), 1.37-1.54(1H, m), 1.78-1.89(2H, m), 2.22(6H, s), 2.46-2.53(1H, m), 2.77-2.86(1H, m), 3.08-3.18(1H, m), 3.18-3.63(8H, m), 3.63-3.75(1H, m), 4.28-4.56(3H, m), 5.66(1H, dd), 6.35(1H, d), 7.01(3H, s), 7.40-7.68(1H, m), 9.88(1H, br) |
| 205 | 354 | 1.22-1.35(1H, m), 1.35-1.54(1H, m), 1.78-1.89(2H, m), 2.02-2.12(1H, m), 2.22(6H, s), 2.48-2.52(2H, m), 2.76-2.87(1H, m), 3.09-3.18(1H, m), 3.28-3.36(3H, m), 3.50-4.10(3H, m), 4.30-4.60(4H, m), 5.65(1H, dd), 6.35(1H, d), 7.01(3H, s), 9.98(1H, br), 10.65(1H, br) |
| 206 | 356 | |
| 207 | 371 | |
| 208 | 343 | |

TABLE 25

| Ex. | MS | NMR |
|---|---|---|
| 209 | 357 | 1.25-1.55(2H, m), 1.81-1.90(2H, m), 2.23(6H, s), 2.48-2.53(1H, m), 2.70-2.85(4H, m), 3.06-3.17(1H, m), 3.32-3.34(2H, m), 3.54-3.63(1H, m), 3.63-3.77(2H, m), 3.93-4.02(1H, m), 4.02-4.44(5H, m), 5.66(1H, dd), 6.36(1H, d), 7.03(3H, s), 9.77(1H, br) |
| 210 | 357 | 1.25-1.55(2H, m), 1.81-1.90(2H, m), 2.23(6H, s), 2.48-2.53(1H, m), 2.70-2.87(4H, m), 3.06-3.18(1H, m), 3.31-3.34(2H, m), 3.54-3.64(1H, m), 3.66-3.77(2H, m), 3.93-4.02(1H, m), 4.02-4.44(5H, m), 5.66(1H, dd), 6.36(1H, d), 7.03(3H, s), 9.77(1H, br) |
| 211 | 371 | 1.20-1.34(1H, m), 1.34-1.54(2H, m), 1.74-1.88(3H, m), 1.93-2.04(1H, m), 2.22(6H, s), 2.42-2.52(1H, m), 2.68(3H, s), 2.70-2.81(1H, m), 2.86-3.04(2H, m), 3.04-3.16(1H, m), 3.50-4.20(6H, m), 4.30-4.40(1H, m), 4.31-4.40(1H, m), 5.65(1H, dd), 6.34(1H, d), 7.01(3H, s) |
| 212 | 399 | |
| 213 | 400 | 1.26-1.38(1H, m), 1.38-1.52(1H, m), 1.80-1.90(2H, m), 2.22(6H, s), 2.45-2.55(1H, m), 2.78-2.94(4H, m), 3.12-3.18(1H, m), 3.18-3.69(12H, m), 3.69-4.03(2H, m), 4.30-4.50(2H, m), 5.65(1H, dd), 6.35(1H, d), 7.01(3H, s) |
| 214 | 327 | |
| 215 | 343 | |
| 216 | 327 | |

TABLE 25-continued

| Ex. | MS | NMR |
|---|---|---|
| 217 | 341 | |
| 218 | 341 | |
| 219 | 341 | |
| 220 | 343 | |
| 221 | 343 | |
| 222 | 343 | |
| 223 | 329 | |
| 224 | 315 | |
| 225 | 357 | |
| 226 | (EI) 271 | |

TABLE 26

| Rf. | Structure |
|---|---|
| 4 | 3,5-dimethyl-4-(hydroxymethyl)biphenyl |
| 5 | (2,6-dimethylbenzyl)triphenylphosphonium chloride |
| 6 | (2-fluoro-6-methylbenzyl)triphenylphosphonium chloride |
| 7 | (2,6-diethylbenzyl)triphenylphosphonium chloride |
| 8 | (2,6-dimethoxybenzyl)triphenylphosphonium chloride |
| 9 | (2,6-difluorobenzyl)triphenylphosphonium chloride |
| 10 | (2-chloro-6-fluorobenzyl)triphenylphosphonium chloride |
| 11 | (2,6-dichlorobenzyl)triphenylphosphonium chloride |
| 12 | (2,4,6-trimethylbenzyl)triphenylphosphonium chloride |
| 13 | (2,6-dimethyl-4-phenoxybenzyl)triphenylphosphonium chloride |
| 14 | (3,5-dimethylbiphenyl-4-ylmethyl)triphenylphosphonium chloride |
| 15 | (4-bromo-2,6-dimethylbenzyl)triphenylphosphonium chloride |
| 17 | (2-chloro-6-methoxybenzyl)triphenylphosphonium bromide |
| 22 | tert-butyl 4-formylpiperidine-1-carboxylate |
| 23 | tert-butyl 3-formylpiperidine-1-carboxylate |

TABLE 26-continued

| Rf. | Stucture |
|---|---|
| 24 | piperidine-N-Boc, 2-carbaldehyde |
| 25 | 1-Boc-azepane-4-carbaldehyde |
| 28 | 3-Me, 4-NC, 1-Bn piperidine |
| 29 | 4-(1-isocyanoethyl)-1-Boc-piperidine (Me, NC) |
| 31 | 1-Bn-piperidine-4-carbaldehyde |
| 32 | 2-(1-Boc-piperidin-4-yl)propanal (Me, O=) |

TABLE 27

| Rf. | Data |
|---|---|
| 1 | NMR: 2.21(3H, s), 5.59(2H, d), 6.99(1H, d), 7.03(1H, d), 7.10(1H, m), 7.59-7.70(12H, m), 7.76-7.80(3H, m) |
| 2 | MS(EI): 262 |
| 3 | MS(EI): 228 |
| 4 | MS(EI): 212 |
| 5 | NMR: 1.78(6H, s), 4.99(2H, d), 6.97(2H, d), 7.13-7.18(1H, m), 7.54-7.59(6H, m), 7.70-7.75(6H, m), 7.91-7.95(3H, m) |
| 6 | NMR: 2.07(3H, s), 5.39(2H, dd), 6.65(1H, t), 6.87(1H, d), 7.10-7.16(1H, m), 7.61-7.72(12H, m), 7.76-7.80(3H, m) |
| 7 | NMR: 0.91(6H, t), 2.14(4H, m), 5.23(2H, d), 6.94(2H, d), 7.19-7.23(1H, m), 7.56-7.66(12H, m), 7.76-7.81(3H, m) |
| 8 | NMR: 3.41(6H, s), 4.62(2H, d), 6.40(2H, d), 7.45(1H, t), 7.40-7.90(15H, m) |
| 9 | NMR: 5.17(2H, d), 7.04(2H, d), 7.45-7.49(1H, m), 7.70-7.77(12H, m), 7.91-7.95(3H, m) |
| 10 | NMR: 5.47(2H, dd), 6.88(1H, t), 7.05(1H, d), 7.20-7.26(1H, m), 7.62-7.82(15H, m) |
| 11 | NMR: 5.14(2H, d), 7.41(3H, m), 7.50-7.85(12H, m), 7.92(3H, m) |
| 12 | NMR: 1.71(6H, s), 2.21(3H, s), 4.91(2H, d), 6.79(2H, s), 7.53-7.58(6H, m), 7.69-7.74(6H, m), 7.90-7.94(3H, m) |
| 13 | NMR(CDCl$_3$): 1.85(6H, s), 5.36(2H, d), 6.54(2H, s), 6.95(2H, d), 7.11(1H, t), 7.34(2H, t), 7.62-7.68(12H, m), 7.76-7.81(3H, m) |
| 14 | NMR(CDCl$_3$): 1.93(6H, s), 5.35(2H, d), 7.11(2H, s), 7.34(1H, t), 7.41(2H, t), 7.51(2H, d), 7.61-7.66(12H, m), 7.76-7.80(3H, m) |
| 15 | NMR: 1.75(6H, s), 4.95(2H, d), 7.22(2H, s), 7.54-7.79(12H, m), 7.89-7.98(3H, m) |
| 16 | NMR: 2.07(3H, s), 3.23(3H, s), 4.97(2H, d), 6.43(1H, d), 6.73(1H, d), 7.14(1H, m), 7.53-7.66(12H, m), 7.77-7.81(3H, m) |
| 17 | NMR: 3.45(3H, s), 5.02(2H, d), 6.64(1H, d), 6.89(1H, d), 7.21(1H, m), 7.58-7.70(12H, m), 7.79-7.83(3H, m) |
| 18 | NMR(CDCl$_3$): 2.38(6H, s), 3.76(3H, s), 6.65(2H, s) |
| 19 | MS: 186 |
| 20 | MS: 130 |
| 21 | NMR(CDCl$_3$): 1.19(2H, m), 1.44(9H, s), 1.67(2H, m), 2.04(1H, m), 2.39(2H, d), 2.74(2H, m), 4.14(2H, m), 9.78(1H, s) |
| 22 | NMR(CDCl$_3$): 1.46(9H, s), 1.51-1.60(2H, m), 1.88(2H, m), 2.39-2.44(1H, m), 2.93(2H, m), 3.97(2H, m), 9.67(1H, s) |
| 23 | NMR(CDCl$_3$): 1.46(9H, s), 1.46-1.60(1H, m), 1.60-1.75(2H, m), 1.90-2.05(1H, m), 2.40-2.50(1H, m), 3.09(1H, ddd), 3.32(1H, dd), 3.60-3.75(1H, m), 9.67(1H, s) |
| 24 | NMR(CDCl$_3$): 1.46(9H, s), 1.70-1.80(1H, m), 1.55-1.75(4H, m), 2.10-2.20(1H, m), 2.80-3.05(1H, m), 3.80-4.15(1H, m), 4.40-4.75(1H, m), 9.59(1H, s) |
| 25 | MS: 226 |
| 26 | MS(EI): 189 |
| 27 | MS: 237 |
| 28 | MS: 215 |
| 29 | MS: 239 |
| 30 | MS: 240 |
| 31 | MS: 218 |
| 32 | MS: 240 |
| 33 | MS(EI): 213 |

TABLE 28
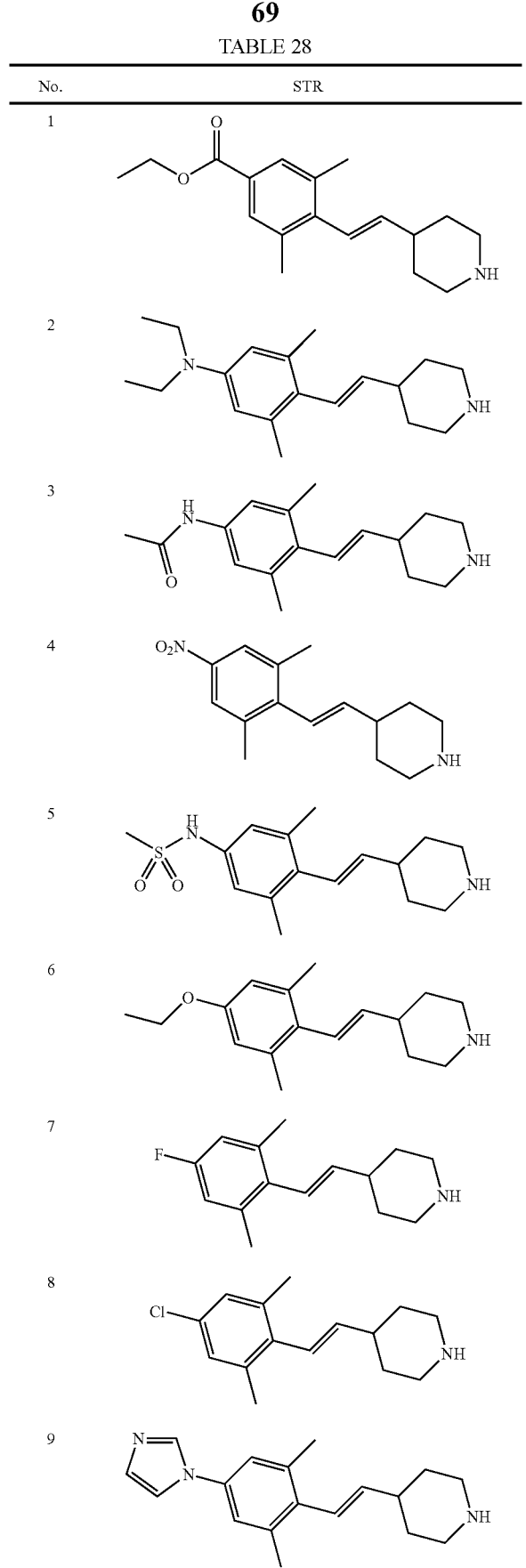
TABLE 28-continued
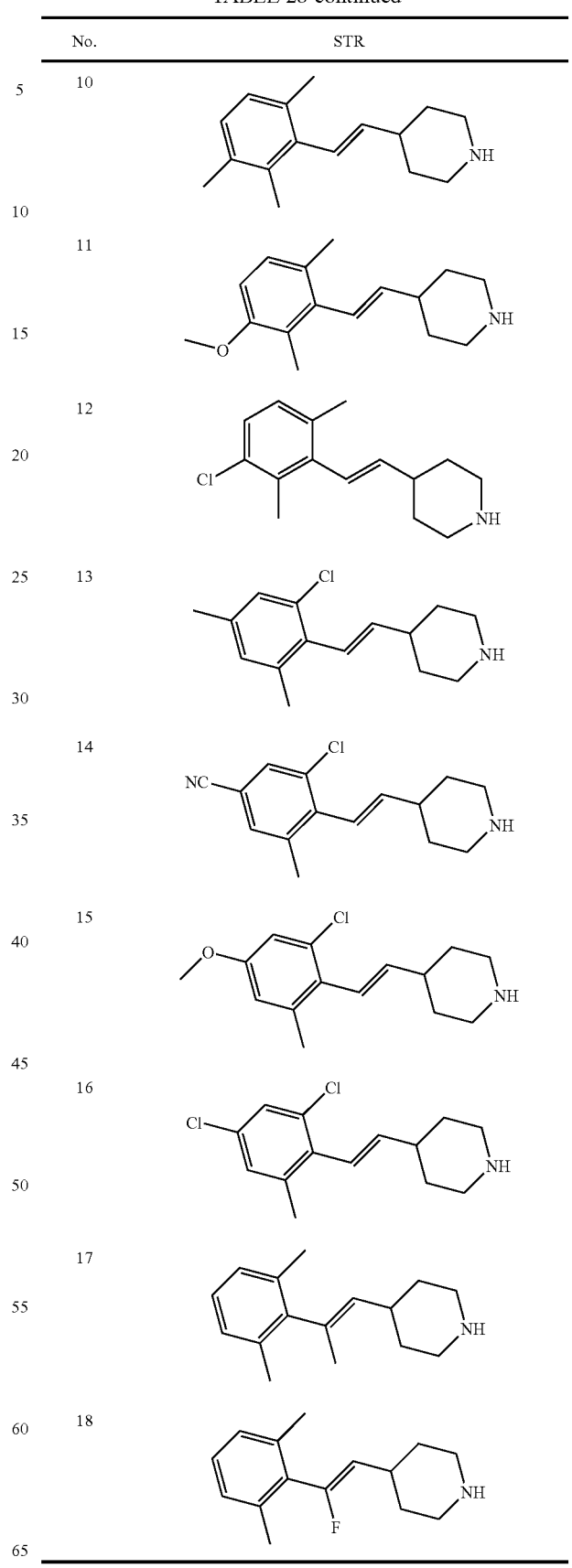

TABLE 29
| No. | STR |
|---|---|
| 19 | 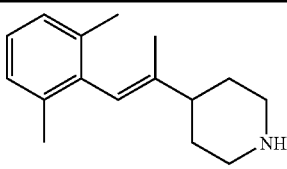 |
| 20 | 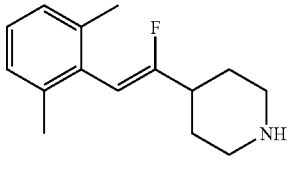 |
| 21 | 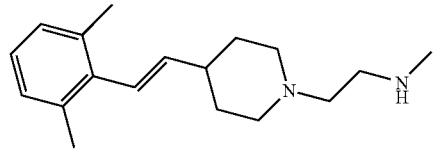 |
| 22 | 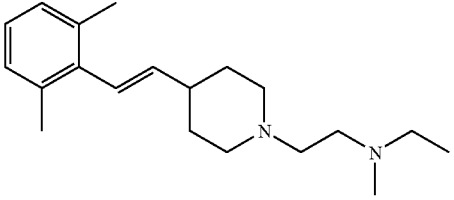 |
| 23 | 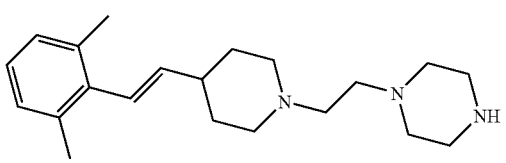 |
| 24 | 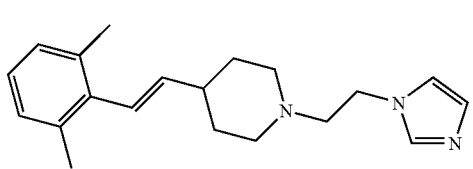 |
| 25 | 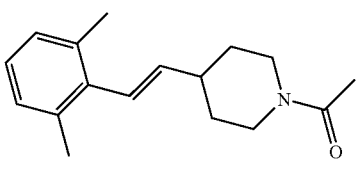 |
| 26 | 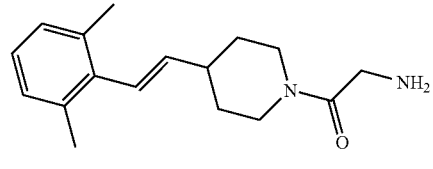 |
| 27 | 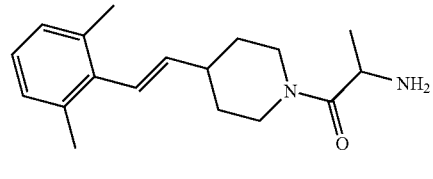 |
TABLE 29-continued
| No. | STR |
|---|---|
| 28 | 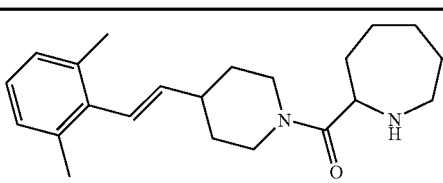 |
| 29 | 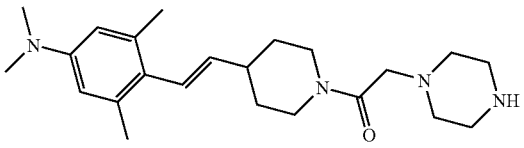 |
| 30 | 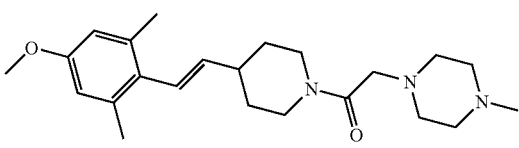 |
| 31 | 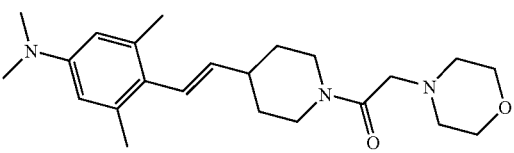 |
| 32 | 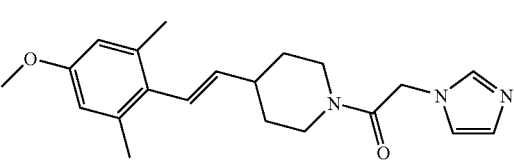 |
| 33 | 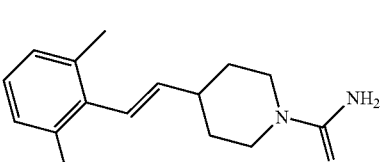 |
| 34 | 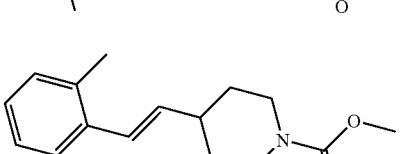 |
| 35 | 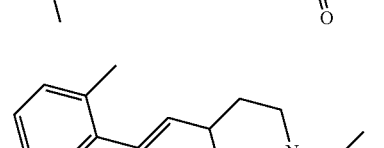 |
| 36 | 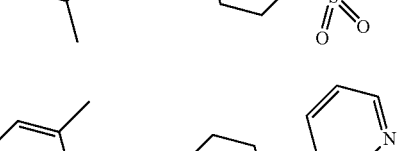 |

TABLE 30

| No. | STR |
|---|---|
| 37 | (structure) |
| 38 | (structure) |
| 39 | (structure) |
| 40 | (structure) |
| 41 | (structure) |
| 42 | (structure) |
| 43 | (structure) |
| 44 | (structure) |

TABLE 30-continued

| No. | STR |
|---|---|
| 45 | (structure) |
| 46 | (structure) |
| 47 | (structure) |
| 48 | (structure) |
| 49 | (structure) |
| 50 | (structure) |
| 51 | (structure) |
| 52 | (structure) |

TABLE 30-continued

| No. | STR |
|---|---|
| 53 | 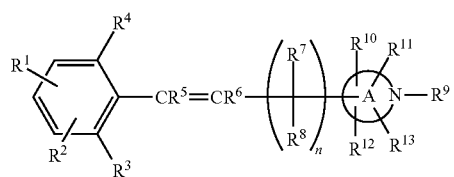 |
| 54 | |

The invention claimed is:

1. A nitrogen-containing heterocyclic derivative represented by formula (I) below:

(I)

wherein symbols in formula (I) above have the following significance:
$R^1$ and $R^2$ represent H—;
$R^3$ and $R^4$, which may be the same or different, represent a lower alkyl;
$R^5$ and $R^6$ represent H—;
$R^9$ represents an optionally substituted acyl, wherein the optionally substituted acyl is an optionally substituted morpholin-4-ylmethylcarbonyl, an optionally substituted 1,4-oxazepan-4-ylmethylcarbonyl, or an optionally substituted piperidin-1-ylmethylcarbonyl, and wherein the substitutent in the optionally substituted acyl is at least one substituent selected from: $R^{101}R^{102}N$, wherein $R^{101}$ and $R^{102}$ represent H; a lower alkyl which may optionally be substituted with OH; and $H_2N$—CO—;

$R^{10}$, $R^{11}$, $R^{12}$ and $R^{13}$ represent H—;
A represents piperidin-4-yl;
n represents 0, or a pharmaceutically acceptable salt thereof.

2. A nitrogen-containing heterocyclic derivative, or a pharmaceutically acceptable salt thereof, which is at least one compound selected from the group consisting of:
   1-(2-{4-[(E)-2-(2,6-dimethylphenyl)vinyl]piperidin-1-yl}-2-oxoethyl)piperidine-2-carboxamide,
   1-(2-{4-(E)-2-(2,6-dimethylphenyl)vinyl]piperidin-1-yl}-2-oxoethyl)-3,5-dimethyl piperidine,
   4-(2-{4-[(E)-2-(2,6-dimethylphenyl)vinyl]piperidin-1-yl}-2-oxoethyl)morpholine,
   [4-(2-{4-[(E)-2-(2,6-dimethylphenyl)vinyl]piperidin-1-yl}-2-oxoethyl)morpholine-2-yl]methanol,
   4-(2-{4-[(E)-2-(2,6-dimethylphenyl)vinyl]piperidin-1-yl}-2-oxoethyl)-1,4-oxazepane, and
   1-(2-{4-[(E)-2-(2,6-dimethylphenyl)vinyl]piperidin-1-yl}-2-oxoethyl)piperidine-4-amine.

3. A pharmaceutical composition comprising the nitrogen-containing heterocyclic derivative according to claim 1, or a pharmaceutically acceptable salt thereof, and a pharmaceutically acceptable carrier.

4. The pharmaceutical composition according to claim 3, which is a sodium channel inhibitor.

5. The pharmaceutical composition according to claim 3, which is a therapeutic agent for neuropathic pain.

6. The pharmaceutical composition according to claim 5, which is a therapeutic agent for diabetic neuropathic pain.

7. The nitrogen-containing heterocyclic derivative according to claim 1, or a pharmaceutically acceptable salt thereof, wherein $R^3$ and $R^4$ are methyl; and the at least one substituent in the optionally substituted acyl shown by symbol $R^9$ in the formula (I) above is at least one substituent selected from: $H_2N$; methyl which may optionally be substituted with OH; and $H_2N$—CO—.

8. The nitrogen-containing heterocyclic derivative according to claim 2, or a pharmaceutically acceptable salt thereof, which is at least one compound selected from the group consisting of:
   (R)-1-(2-{4-[(E)-2-(2,6-dimethylphenyl)vinyl]piperidin-1-yl}-2-oxoethyl)piperidine-2-carboxamide,
   (S)-1-(2-{4-[(E)-2-(2,6-dimethylphenyl)vinyl]piperidin-1-yl}-2-oxoethyl)piperidine-2-carboxamide,
   (R)-[4-(2-{4-[(E)-2-(2,6-dimethylphenyl)vinyl]piperidin-1-yl}-2-oxoethyl)morpholine-2-yl]methanol, and
   (S)-[4-(2-{4-[(E)-2-(2,6-dimethylphenyl)vinyl]piperidin-1-yl}-2-oxoethyl)morpholine-2-yl]methanol.

* * * * *